United States Patent
Sobel et al.

(10) Patent No.: US 11,674,938 B2
(45) Date of Patent: Jun. 13, 2023

(54) UTILIZATION OF ELECTRONIC NOSE-BASED ANALYSIS OF ODORANTS

(71) Applicant: Yeda Research and Development Co. Ltd., Rehovot (IL)

(72) Inventors: Noam Sobel, Jaffa (IL); Shani Agron, Rehovot (IL); Kobi Snitz, Rehovot (IL); Ethan Livne, Rehovot (IL); Ofer Perl, Rehovot (IL); Kineret Weissler, Rehovot (IL); Aharon Ravia, Rehovot (IL); Danielle Ricca Honigstein, Rehovot (IL); Maya Finkel, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 16/894,916

(22) Filed: Jun. 8, 2020

(65) Prior Publication Data
US 2020/0300829 A1 Sep. 24, 2020

Related U.S. Application Data

(63) Continuation of application No. PCT/IL2018/051341, filed on Dec. 9, 2018.
(Continued)

(51) Int. Cl.
*G01N 33/00* (2006.01)

(52) U.S. Cl.
CPC ..... *G01N 33/0036* (2013.01); *G01N 33/0031* (2013.01)

(58) Field of Classification Search
CPC ........... G01N 33/0036; G01N 33/0031; G01N 33/0001; G01N 33/0034; G01N 1/405;
(Continued)

(56) References Cited

U.S. PATENT DOCUMENTS

| 7,167,815 B2 * | 1/2007 | Labreche ........... G01N 33/0034 |
| | | 702/193 |
| 7,593,863 B1 | 9/2009 | Sunshine et al. |

(Continued)

FOREIGN PATENT DOCUMENTS

| CN | 1967594 | 5/2007 |
| CN | 101788517 | 7/2010 |

(Continued)

OTHER PUBLICATIONS

A Review of The science and Technology of Odor Measurement (Year: 2005).*
(Continued)

*Primary Examiner* — Catherine T. Rastovski
*Assistant Examiner* — Kaleria Knox

(57) ABSTRACT

A method of assessing odors, comprises providing an electronic nose that extracts measurements from odors, from which measurements at least n chemical descriptors are extracted where n is greater than unity, and typically around 18. The electronic nose is applied to an odor, and odor information is extracted. The information is plotted to a first location on an n-dimensional sample space, each dimension being related to a respective one of the n chemical descriptors or otherwise optimized for the particular enose and the measurements it makes; and an assessment of the odor is provided based on the plotted location. The assessment may be a description based on odor describing terms, or may be a chemical description in terms of chemicals that can synthesize the odor, and the odor may then be synthesized based on the chemical description.

23 Claims, 15 Drawing Sheets
(7 of 15 Drawing Sheet(s) Filed in Color)

Related U.S. Application Data

(60) Provisional application No. 62/596,140, filed on Dec. 8, 2017.

(58) Field of Classification Search
CPC ..... G01N 33/0062; G06F 17/00; G06F 15/00; A61B 5/00; D06F 34/14; G06N 20/00; G06Q 30/0203
See application file for complete search history.

(56) References Cited

U.S. PATENT DOCUMENTS

| | | | | |
|---|---|---|---|---|
| 8,443,647 | B1 * | 5/2013 | Kolmakov | ........... G01N 27/127 73/1.02 |
| 8,880,448 | B2 * | 11/2014 | Haddad | .............. G01N 33/0073 512/1 |
| 10,416,138 | B2 * | 9/2019 | Byron | ................ G01N 33/0001 |
| 2005/0208673 | A1 | 9/2005 | Labreche et al. | |
| 2008/0021763 | A1 * | 1/2008 | Merchant | ........... G06Q 30/0203 705/7.32 |
| 2012/0143804 | A1 * | 6/2012 | Haddad | ................. G06N 20/00 706/20 |
| 2013/0236417 | A1 | 9/2013 | Ray et al. | |
| 2016/0216244 | A1 * | 7/2016 | Sobel | ................ G01N 33/0031 |

FOREIGN PATENT DOCUMENTS

| | | |
|---|---|---|
| EP | 0632268 | 1/1995 |
| JP | 2003-279459 | 10/2003 |
| JP | 2005-241642 | 9/2005 |
| JP | 2009-156768 | 7/2009 |
| JP | 2007-309752 | 11/2009 |
| JP | 2009-300188 | 12/2009 |
| WO | WO 01/07094 | 2/2001 |
| WO | WO 2011/010312 | 7/2011 |
| WO | WO 2015/037003 | 3/2015 |
| WO | WO 2019/111262 | 6/2019 |

OTHER PUBLICATIONS

McGinley "Odor Basis", Understanding and Using Odor Testing (Year: 2000).*
International Preliminary Report on Patentability dated Jun. 18, 2020 From the International Bureau of WIPO Re. Application No. PCT/IL2018/051341. (15 Pages).
International Search Report and the Written Opinion dated May 29, 2019 From the International Searching Authority Re. Application No. PCT/IL2018/051341. (23 Pages).
Invitation to Pay Additional Fees. Communication Relating to the Results of the Partial International Search and the Provisional Opinion dated Apr. 3, 2019 From the International Searching Authority Re. Application No. PCT/IL2018/051341. (13 Pages).
Burl et al. "Assessing the Ability to Predict Human Percepts of Odor Quality From the Detector Responses of A Conducting Polymer Composite-Based Electronic Nose", Sensor & Actuators: B Chemical, XP004228226, 72(2): 149-159, Jan. 25, 2001.
Le Berre et al. "Just Noticeable Differences in Component Concentrations Modify the Odor Quality of A Blending Mixture", Chemical Senses, XP055570957, 33(4): 389-395, Advance Access Publication Feb. 27, 2008.
Santos et al. "Comparison Between An Electronic Nose and A Human Sensory Panel for Wine Compound Detection", Proceedings of IEEE Sensors Conference 2004, Vienna, Austria, Oct. 24-27, 2004, XP055570927, p. 341-344, Oct. 24, 2004.
Translation of Notification of Office Action and Search Report dated May 19, 2022 From the State Intellectual Property Office of the People's Republic of China Re. Application No. 201880088963.8. (16 p[ages).
Notification of Office Action and Search Report dated May 19, 2022 From the State Intellectual Property Office of the People's Republic of China Re. Application No. 201880088963.8. (12 Pages).
English Translation dated Oct. 19, 2022 of Notification of Office Action and Search Report dated Oct. 14, 2022 From the China National Intellectual Property Administration Re Application No. 201880088963.8. (12 Pages).
Notification of Office Action and Search Report dated Oct. 14, 2022 From the China National Intellectual Property Administration Re. Application No. 201880088963.8. (7 Pages).
Public Evidence CPEL2051407P. "100 Questions in Science in Life" Editor office of Science and Technology Daily, Beijing Institute of Technology Press; Jun. 30, 2011; pp. 288-290.
Communication Pursuant to Rule 164(2)(b) and Article 94(3) EPC dated Dec. 13, 2022 From the European Patent Office Re. Application No. 18830316.8.(10 pages).
Dymerski et al. "Invited Review Article: An Odor-Sensinq System—powerful Technique for Foodstuff Studies", Review of Scientific Instiuments 82(111101): 132, Nov. 30, 2011.
Notice of Reason(s) for Rejection dated Feb. 15, 2023 From the Japan Patent Office Re. Application No. 2020-530335. (7 pages).
Translation Dated Mar. 7, 2023 of Notice of Reason(s) for Rejection dated Feb. 15, 2023 From the Japan Patent Office Re. Application No. 2020-530335. (6 pages).

* cited by examiner

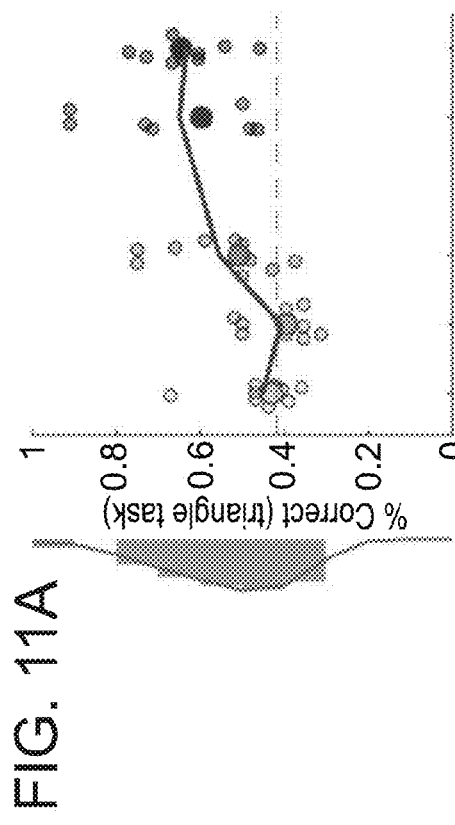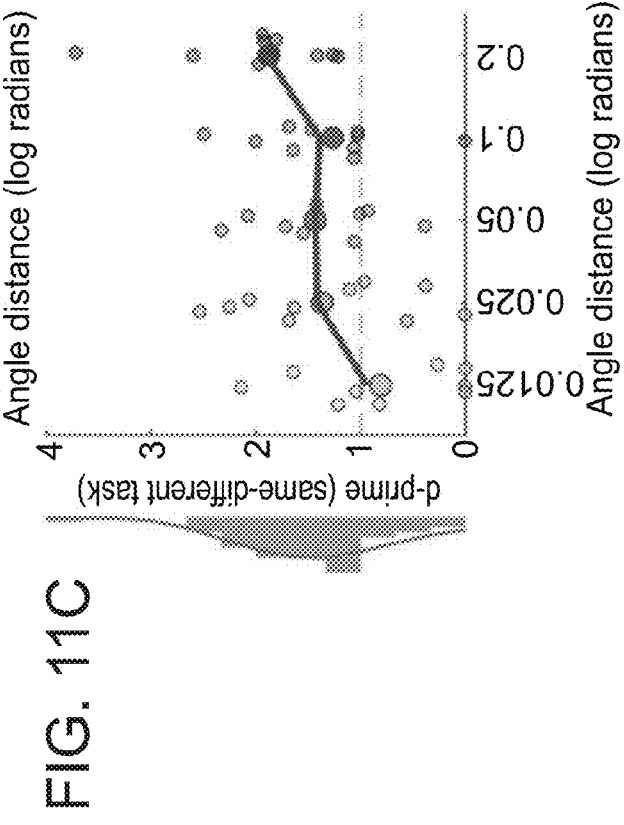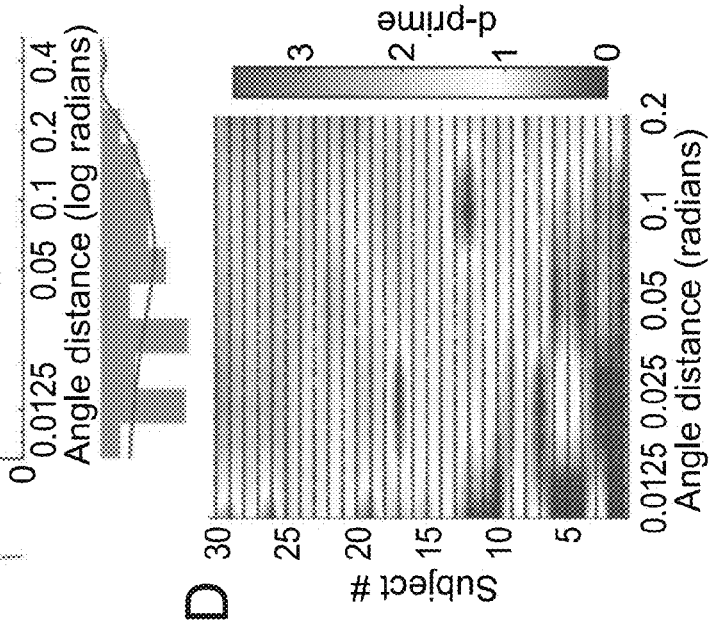
FIG. 11A  FIG. 11B  FIG. 11C  FIG. 11D

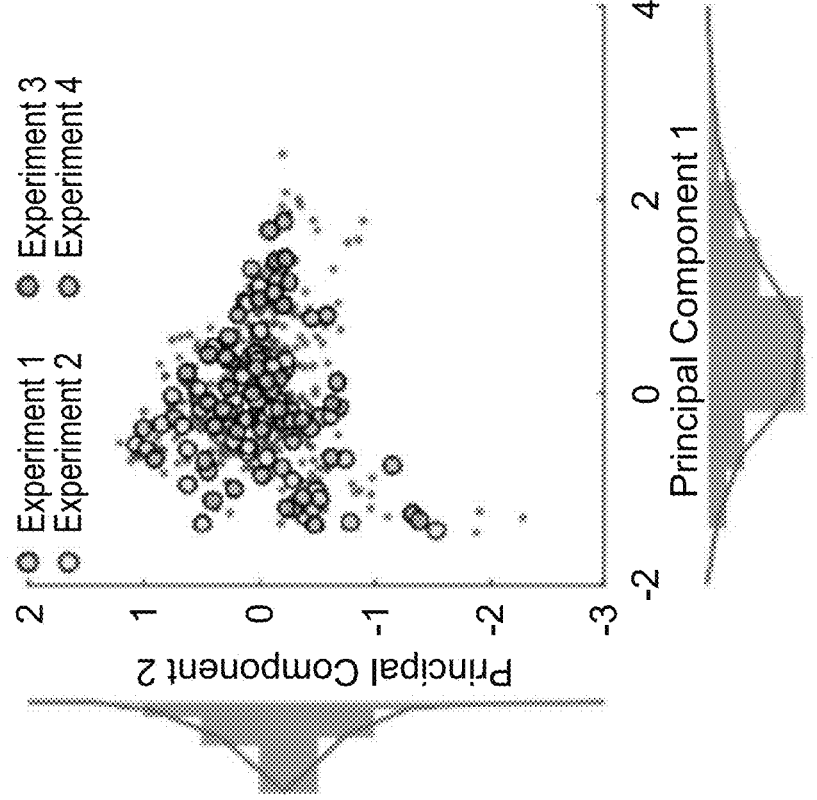
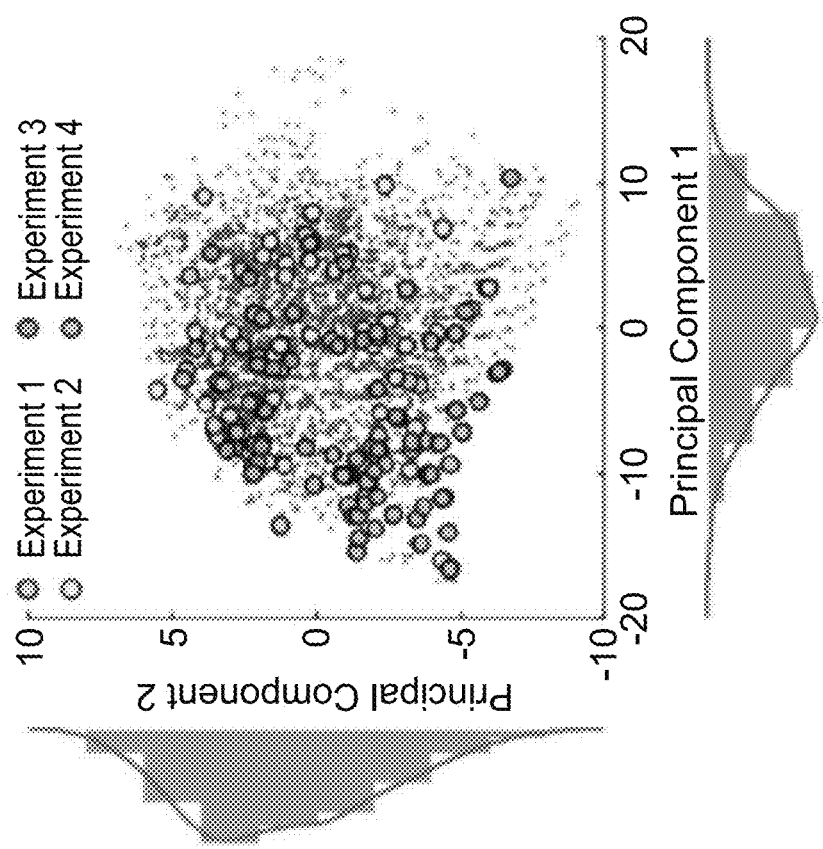

UTILIZATION OF ELECTRONIC NOSE-BASED ANALYSIS OF ODORANTS

RELATED APPLICATIONS

This application is a Continuation of PCT Patent Application No. PCT/IL2018/051341 having international filing date of Dec. 9, 2018, which claims the benefit of priority under 35 USC § 119(e) of U.S. Provisional Patent Application No. 62/596,140 filed on Dec. 8, 2017. The contents of the above applications are all incorporated by reference as if fully set forth herein in their entirety.

FIELD AND BACKGROUND OF THE INVENTION

The present invention, in some embodiments thereof, relates to utilization of electronic nose-based analysis of odorants and, more particularly, but not exclusively, to a way of communicating an analysis of an odorant directly or synthesizing the odorant for indirect communication or other purposes.

In 1968, Dravnieks envisioned an artificial or electronic nose as an instrument that would inspect samples of odorous air and report the intensity and quality of an odor without the intervention of a human nose. Although eNoses have since been developed, they serve primarily in tasks of odor detection and discrimination but not for reporting odor quality.

The main component of an eNose is an array of non-specific chemical sensors. An odor analyte stimulates many of the sensors in the array and elicits a characteristic response pattern. The sensors inside eNoses can be made of a variety of technologies, but in all cases a certain physical property is measured and a set of signals is generated. The stages of the recognition process are similar to those of biological olfaction, where a sensor responds to more than one odorant and one odorant activates more than one sensor. Together, the set of activated sensors and their signals characterize the odor, sometimes referred as an odor fingerprint. Thus, an important difference between eNoses and analyte detectors such as gas chromatographs, is that whereas the latter are aimed at identifying the components that contribute to an odor, eNoses can be used to identify, as a whole, the mixture of components that together form an odor. Despite the promise of an artificial system that may substitute for olfaction, very few efforts have been made to use eNoses in tasks that go beyond detection and discrimination. A notable exception are the efforts to develop eNoses for medical diagnosis. In such efforts, eNoses were used to identify the disease as a whole, rather than particular analytes that relate to it. In a previous proposal, the present inventors linked eNose measurements to olfactory activity in olfactory receptor neurons suggesting that an eNose can capture the odor attributes relevant to biological receptors. Subsequently, U.S. Pat. No. 8,880,448 Predicting Odor Pleasantness set out to ask whether eNose measurements can in any way be linked to olfactory perception. This effort may be more complicated than linking eNose output to receptor response. Because perception is governed not only by stimulus structure, but also by higher-order mechanisms such as experience and learning.

Similarly, Burl et al 2001 attempted to report perceptual qualities using an eNose. Using an array of conducting polymer composite detectors, they predicted 17 odor qualities for each of 20 odorants by using a "leave one out" scheme, and a battery of prediction algorithms. Although significant prediction rates were obtained for a portion of the odor qualities, the result did not generalize to novel odorants. Burl et al (Burl et al. 2001) postulated that this outcome may have reflected the small number of odorants they used.

Burl et al (Burl et al. 2001) focused their efforts on predicting discreet perceptual characteristics, for example minty and floral. In above mentioned U.S. Pat. No. 8,880,448, a solution was applied to electronic nose measurements of an odor that involved extracting odor information using the electronic nose, and plotting the extracted odor information onto a location on an axis of odor pleasantness, where the axis is formed using a neural network. The neural network is formed according to experiments in which human testers assessed the particular odors.

A problem with the above is that a number or description in words on a one-dimensional axis is not a very meaningful way of conveying information about an odor, and certainly does not provide enough information to allow a given odor to be replicated. A one-dimensional axis may allow rating of an odor according to say pleasantness, but there is much more to an odor than pleasantness.

SUMMARY OF THE INVENTION

The issues in the prior art are addressed by using a multi-dimensional sample space to represent the odors as measured by the electronic nose. The multi-dimensional sampling space may be based on or optimized for the features measured by the electronic nose.

Then a description may be provided by selection of natural language templates based on a position of the measurement in the sample space, or specifically the proximity of the measurement in the sample space to known samples.

Likewise, a synthesis of the odor may be obtained by using a mixture of chemicals wherein the mixture is indicated by the location of the measurement in a multi-dimensional sample space.

The multi-dimensional sampling space and/or the description may be used to bring in the sense of smell to the issue of the Just Noticeable Difference (JND). The smallest perturbation a sensory system can detect is its JND. JNDs are important for sensory neurobiology because they imply the minimal requirements for neural sensors and circuits. JNDs are also important for technology, as they determine the resolution for digitization. JNDs have been identified for visual and auditory qualities, but not for odor quality. To define an odor quality JND, a reproducible physicochemical measure of smell may be used, and the present embodiments may provide a candidate.

According to an aspect of some embodiments of the present invention there is provided a method of assessing odors, comprising:

providing an electronic nose that extracts measurements from odors, from which measurements at least n chemical descriptors are extractable where n is greater than unity;

applying the electronic nose to an odor;

extracting odor information of the odor using the electronic nose;

plotting the extracted odor information to a first location on an n-dimensional sample space, each dimension being related to a respective one of the n chemical descriptors; and outputting an assessment based on the first location.

An embodiment may involve selecting the n chemical descriptors from m chemical descriptors available from the electronic nose, where m is greater than n.

An embodiment may involve selecting the n chemical descriptors that build a sample space on which test odors identified to be similar cluster relatively close together and test odors identified to be different are relatively far apart.

In an embodiment, the sample space may have a plurality of test samples plotted thereon, each sample being associated with at least one odor describing term. The method may find a predetermined number of closest test samples to the first location or may find all test samples within a predetermined radius of the first location and the outputting an assessment may comprise outputting an odor describing term associated with the test samples thus found.

Alternatively, the sample space may have a plurality of regions, and the method may involve associating respective regions of the sample space with corresponding odor describing terms. Outputting an assessment may involve outputting an odor describing term associated with the first location.

In embodiments, the regions are locations in the sample space of test odors and the terms are terms associated with the test odors. Embodiments may comprise selecting a predetermined number of most commonly occurring odor describing terms.

The predetermined number may for example be 5.

An embodiment may comprise providing templates for odor-related discourse, and inserted the odor-describing term associated with the first location into one of the templates.

The sample space may have a plurality of regions, the method comprising:
associating respective regions of the sample space with corresponding odor carrying chemicals, and the outputting an assessment comprises outputting details of one or more odor-carrying chemicals having regions on or close to the first location.

The method may synthesize the odor using the odor-carrying chemicals defined in the details.

In embodiments, n is 18.

An embodiment comprises finding a just noticeable distance between odors on the perception space, the just noticeable distance being an average of minimum discernable distances over a group of users.

An embodiment comprises digitizing the perception space based on the just noticeable distances.

An embodiment comprises using the digitizing to provide a measurement of an input odor.

An embodiment comprises using the digitizing to provide a comparison between different odors.

According to a second aspect of the present invention there is provided a digital electronic nose comprising:
an n-dimensional digitized perception space, the space digitized in terms of just noticeable distances, the just noticeable distances being an average of minimum discernable distances over a group of users;
an input for an odor to be measured;
a mapping unit connected to the input and to the n-dimensional digitized perception space, for mapping the input odor onto a first location on the digitized n-dimensional perception space, the first location being expressible digitally in terms of the just noticeable distances;
an output for outputting a digitized measure of the input odor based on the first location expressed in terms of the just noticeable distances.

In embodiments, the n-dimensional perception space is electronically stored.

In embodiments, the n-dimensional perception space comprises physicochemical descriptors applied to molecules along n axes of smell, wherein n is a plural integer.

In embodiments, respective just noticeable distances are angles on the n-dimensional perception space.

In embodiments, an angle between two odors on the n-dimensional digitized perception space is $$\arccos\left(\frac{\vec{u}\cdot\vec{v}}{|\vec{u}|\cdot|\vec{v}|}\right)$$

where $\vec{u}\cdot\vec{v}$ is the dot product between vectors representing the two odors respectively and $|\vec{u}||\vec{v}|$ are their Euclidean norms.

In embodiments, the molecules in the perception space are weighted according to $$W(X) = \frac{1}{1+e^{\frac{x-1.3}{0.07}}}$$

where x is a normalized intensity.

According to a third aspect of the present invention there is provided a method of assessing odors, comprising:
providing an electronic nose that extracts chemical characterizations from odors;
applying the electronic nose to first and second odors;
extracting a chemical odor characterization of the first and second odors respectively using the electronic nose;
measuring a distance between respective chemical odor characterizations of the first and second odors; and
outputting the distance as a measure of similarity between the first and second odors.

Embodiment may comprise digitization of the distance in terms of just noticeable differences.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a simplified flow chart showing the detection of an odor and its plotting on an n-dimensional sample space as a way of providing a description, according to an embodiment of the present invention;

FIG. 2 is a simplified diagram showing apparatus for carrying out the method or FIG. 1;

FIG. 3 is a simplified flow chart showing a method for providing a textual description of an odor according to an embodiment of the present invention;

FIG. 4 is a graph showing descriptors applied using the present embodiments as compared with descriptors applied using human testers;

FIG. 5 is a simplified diagram showing a process of synthesizing an odor according to the present embodiments;

FIG. 6 is a simplified diagram showing modeling of similar mixtures on a chemical sample space according to the present embodiments;

FIG. 7 is a simplified diagram showing angle distance between modeled results and chemical data;

FIGS. 8A-8F are simplified graphs showing how the similarity of smell measured according to the present embodiments predicts similarity of real world odorant mixtures;

FIGS. 9A-9D are simplified graphs showing how the measure of smell according to the present embodiments predicts the perceived similarity of rose, violets, and asafoietida;

FIGS. 10A-10C are a sequence of graphs showing how the measure of smell according to the present embodiments predicts performance in olfactory discrimination tasks;

FIGS. 11A-11D are a sequence of graphs illustrating how a figure for the odor quality JND according to the present embodiments may be arrived at;

Figure 14:
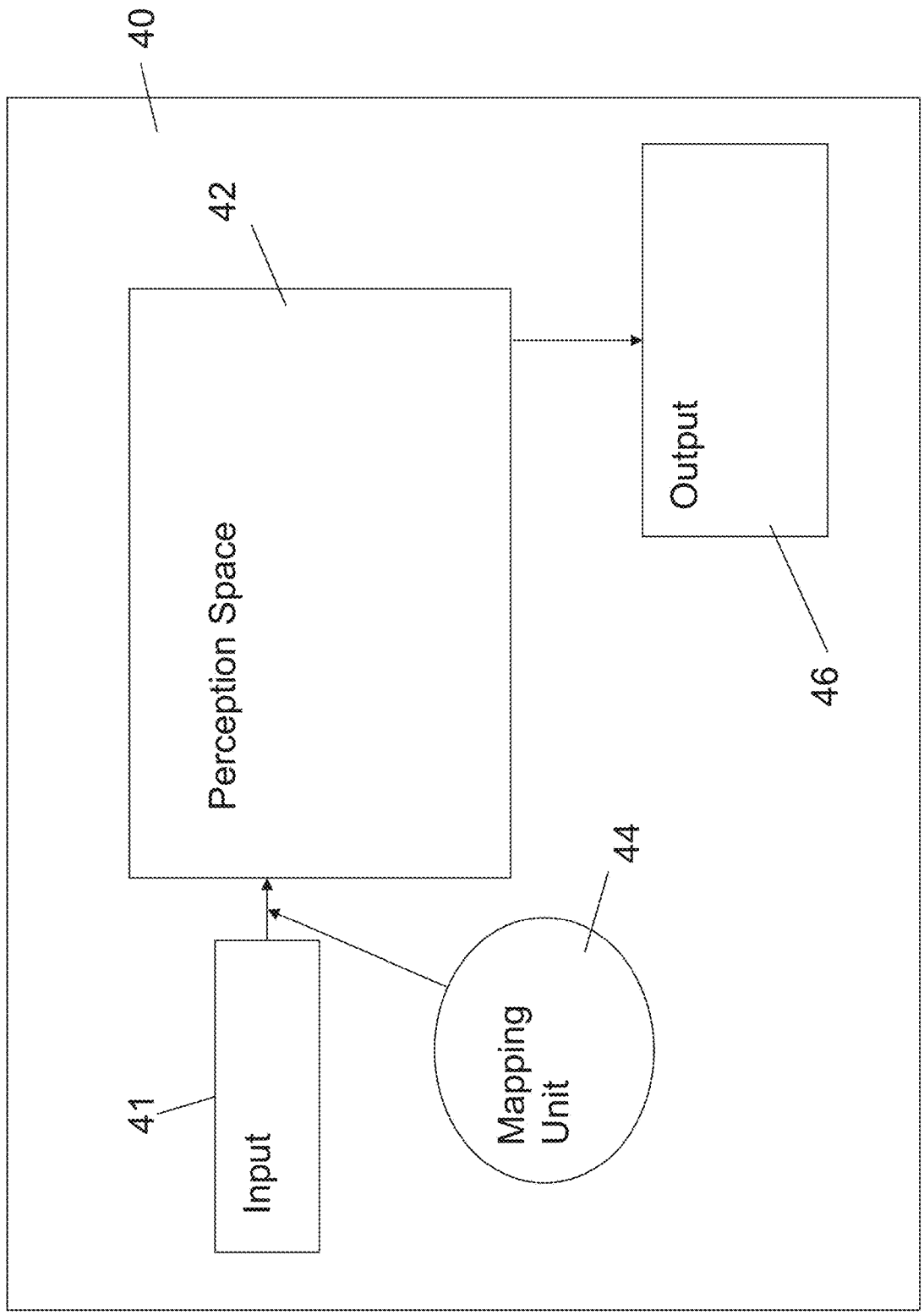
Figure 15:
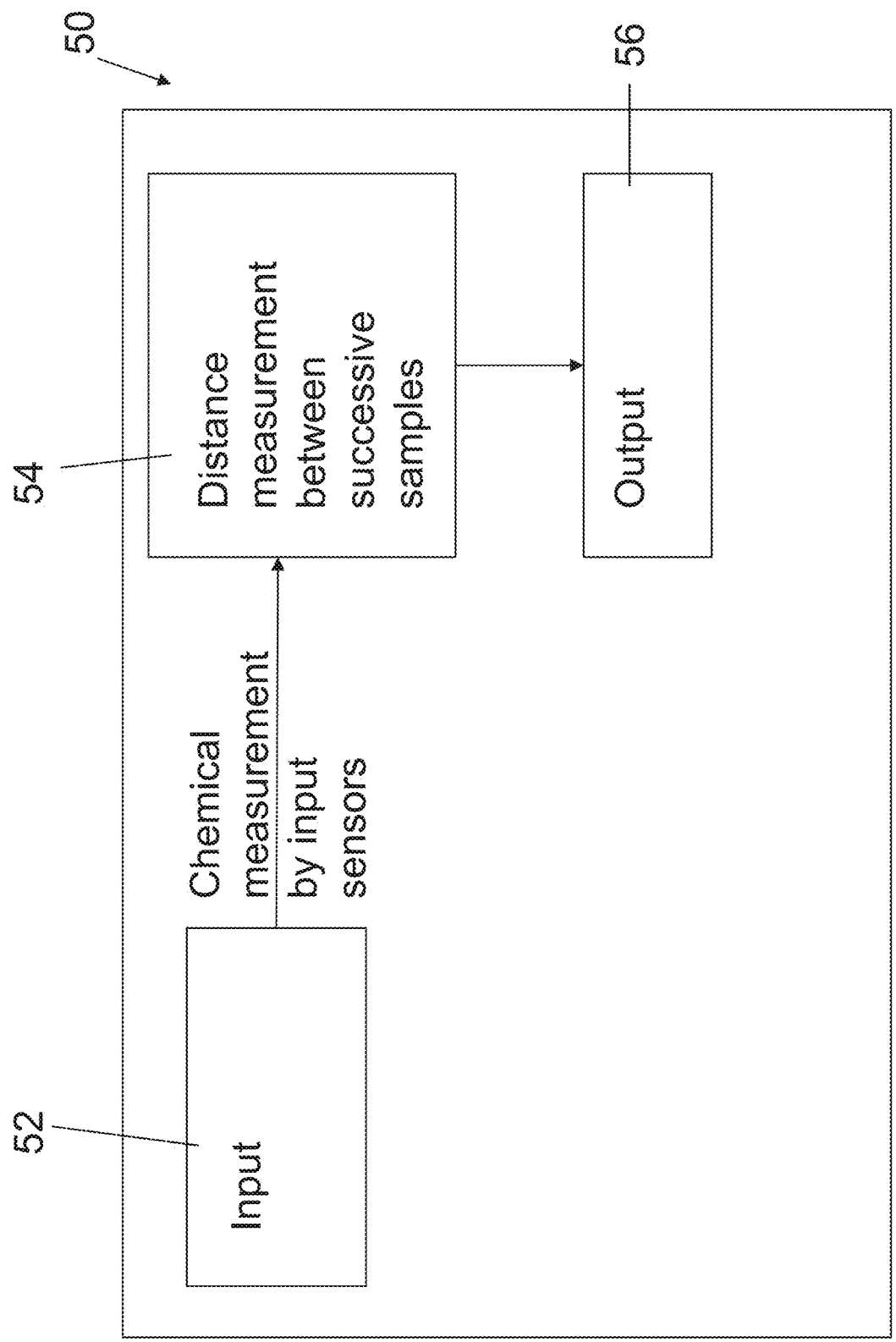

FIGS. 12A and 12B are two graphs illustrating the odors used in experiments to do with the present embodiments wherein the odors used are projected into perceptual space;

FIGS. 13A to 13D are four graphs illustrating how angular distance between odors measured according to the present embodiments translates to perceived similarity;

FIG. 14 is a block diagram showing a digital enose according to embodiments of the present invention; and FIG. 15 is a block diagram showing a further enose according to embodiments of the present invention that may be used to produce either digital or analog output.

DESCRIPTION OF SPECIFIC EMBODIMENTS OF THE INVENTION

The present invention, in some embodiments thereof, relates to a way of utilizing the measurements of an odor that may be obtained from an electronic nose.

A method of assessing odors, comprises providing an electronic nose that extracts measurements from odors, from which measurements at least n chemical descriptors are extractable where n is greater than unity; applying the electronic nose to an odor; extracting odor information of the odor using the electronic nose; plotting the extracted odor information to a first location on an n-dimensional sample space, each dimension being related to a respective one of the n chemical descriptors or otherwise optimized for the particular enose and the measurements it makes; and outputting an assessment based on the plotted location. The assessment may be a description based on odor describing terms, or may be a chemical description in terms of chemicals that can synthesize the odor, and the odor may then be synthesized based on the chemical description.

Furthermore, the present embodiments may extend to optimizing the measure, for example expressed in radians, that accurately reflects the perceptual similarity or difference between any two odorants based on their structure alone. In a trial, 166 participants conducted 38,744 trials rating odorant mixtures systematically varying in their distance along the measure. It was observed in the trial that the smallest difference in odor quality that humans can detect, i.e. the olfactory JND, is 0.0125 radians between odorants. Beyond implications for neurobiology and technology, this framework paves a path to define smells and thus assert rights such as copyrights on particular smells.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
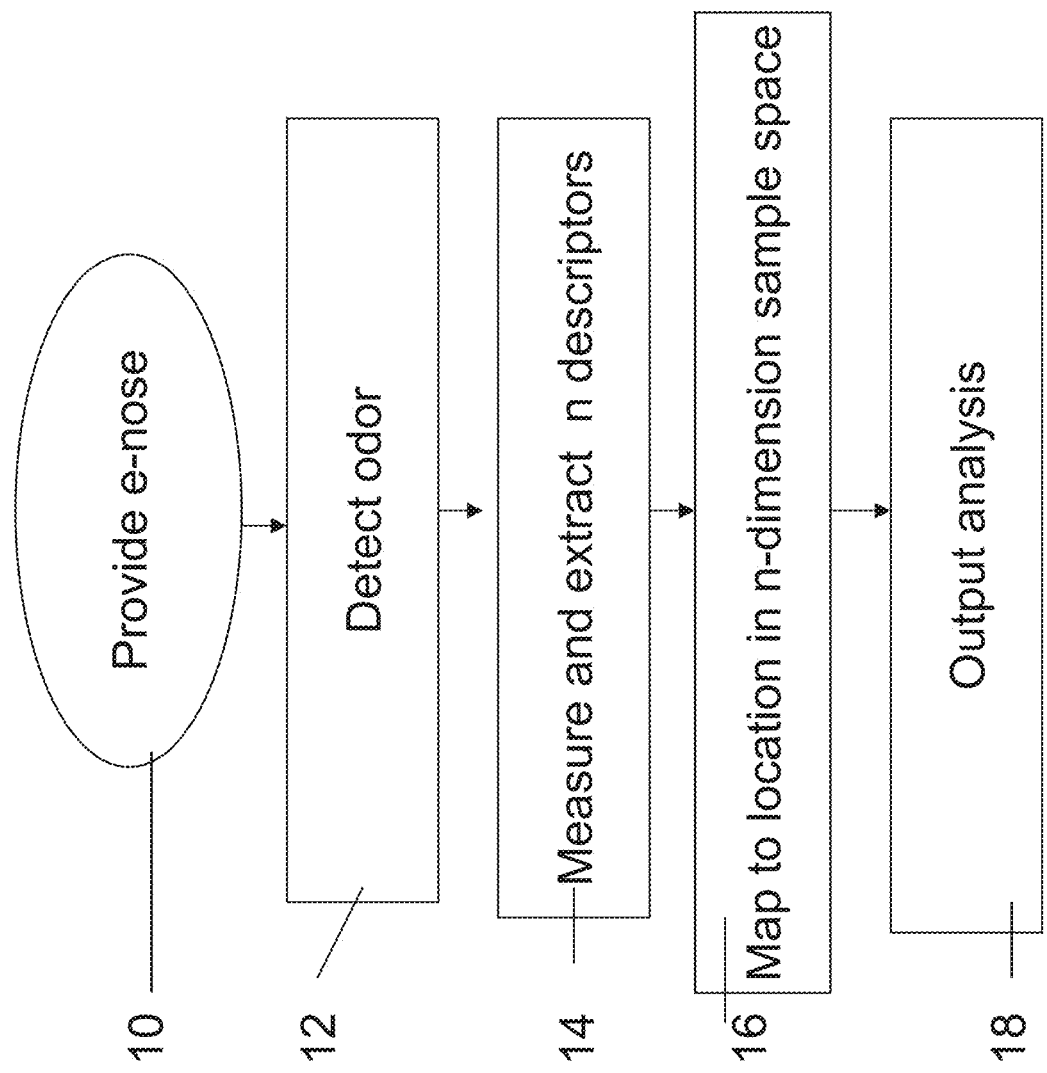

Referring now to the drawings, FIG. 1 illustrates a method of assessing odors, that provides an electronic nose—10. The term "electronic nose" refers to any device designed for measuring gaseous chemical content of a sample of air or other gas and includes a device that identifies the specific components of an odor and analyzes its chemical makeup to identify it. An electronic nose may consist of a mechanism for chemical detection, such as an array of electronic sensors, and a mechanism for pattern recognition, such as a neural network. Descriptors of the odor may then be extracted either from the sensors themselves or from the pattern recognition.

The electronic nose according to the present embodiments detects an odor—12—and extracts measurements from which descriptors are obtained—14. In the present embodiments the measurements are used to provide at least n chemical descriptors that may be extracted where n is an integer greater than one. A typical number of descriptors that may be used is 18. In general, using fewer descriptors makes the result less meaningful and using more descriptors makes the process slower without adding very much useful meaning. The number 18 was found to be optimal based on the measurements obtained from a specific nose. However, other numbers of descriptors may be optimal depending on the nose used, and sub-optimal solutions may be selected by the skilled person based on other considerations.

Once the descriptors are available, the odor is plotted —16—at a first location on an n-dimensional sample space, where each dimension is related to a particular one of the n chemical descriptors. An assessment is then output —18— based on the location in the sample space.

The electronic nose generally extracts large numbers of measurements, but some relate to odor constituents that are less perceived by humans and some relate to odor constituents that are more strongly perceived by humans. Furthermore, some descriptors may be very similar to others so that they could be left out with very little overall effect. Either way, not all of the possible descriptors are needed and the present embodiments may involve selecting the n chemical descriptors from the larger group of m chemical descriptors available from the electronic nose. As will be discussed in greater detail below, the sample space may be initially constructed using a predefined set of odors and a group of human testers. The human testers decide which odors are similar and which not, and various combinations of n descriptors are then tested to see which combination best causes the similar odors to cluster together and the different odors to be distant from each other. A set of n descriptors which best agrees with the assessment of the testers is chosen as the basis for the n-dimensional sample space.

Once the sample space is defined, the test samples are defined thereon and each test sample has some descriptive terms associated with it. The new sample is plotted in the space and the nearest test samples are found. The nearest test samples may be the nearest k samples, or they may be any samples within a given radius. The terms associated with the test samples that have been found may be used to describe the current odor.

Alternatively, the sample space may be divided into regions. The regions may be arbitrary or may be based on the clustering already known about, say from the testing. The different regions are then provided with odor describing terms, say which the testers have found to be descriptive of the odors clustering in the particular region. It is stressed that a given region may have several terms associated with it, and likewise a single term may be associated with several regions. The assessment output for any odor subsequently measured may then be based on the terms associated with the region in which the odor is plotted in the sample space.

As will be described in greater detail below, templates for odor-related discourse may be provided. These templates include sentences used in discussions about odor—and have blanks for the actual odor-describing term. The assessment may then involve inserting the extracted term or terms into an appropriate template. In this way the assessment gives the impression of being produced by a human.

As discussed below, an alternative it is to associate regions with odor-carrying chemicals. As above a single region may be associated with more than one chemical and a given chemical may be associated with more than one region. An input odor is plotted on the sample space and then may be described in terms of the chemicals associated with the plot location or those chemicals in the immediate surroundings. The input odor may then by synthesized by using the chemicals in the description.

Figure 2:
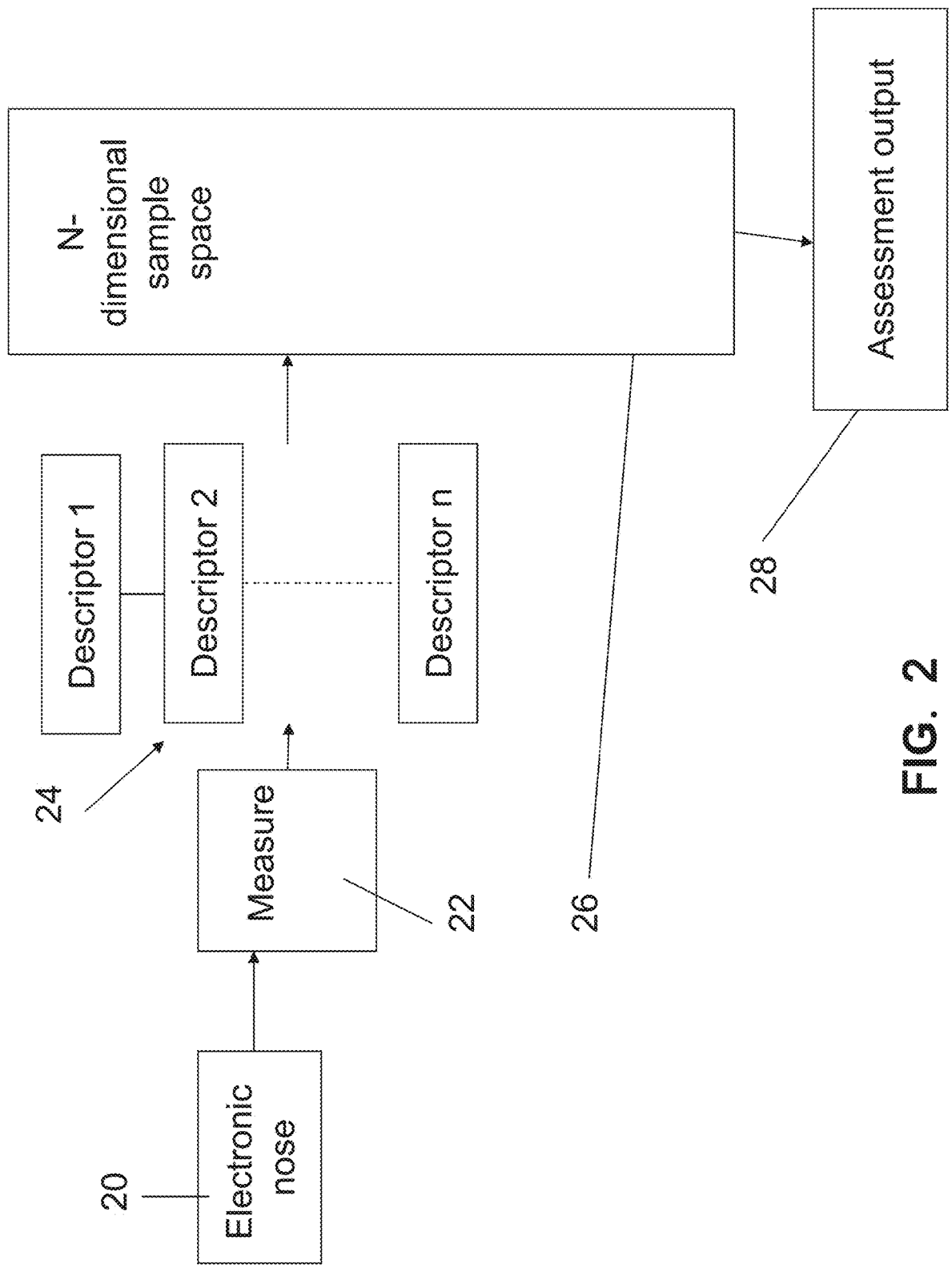

Referring to FIG. 2, an electronic nose 20 measures a sample and produces measurements 22. The measurements 22 produce descriptors 1 . . . n 24, which are then mapped onto an n-dimensional sample space 26, and an assessment output is then provided 28 based on the location in the sample space where the odor is plotted based on the n descriptors.

The embodiments are now described in greater detail. Firstly, the embodiment in which a verbal description is provided is discussed, and an aim is to pass the Turing test for nose in that humans will be unable to tell that the description of the odor has in fact come from a machine.

An aim of the embodiment is to present an electronic nose (enose) with an unknown sample. The machine analyzes the sample and produces a description of the odor of the sample in free text as if it was given by a person. The descriptions produced by the machine may be intended to be indistinguishable from those provided by test subjects. A confirmation of the result would amount to the machine passing an olfactory version of the Turing test, the so-called imitation game.

Figure 3:
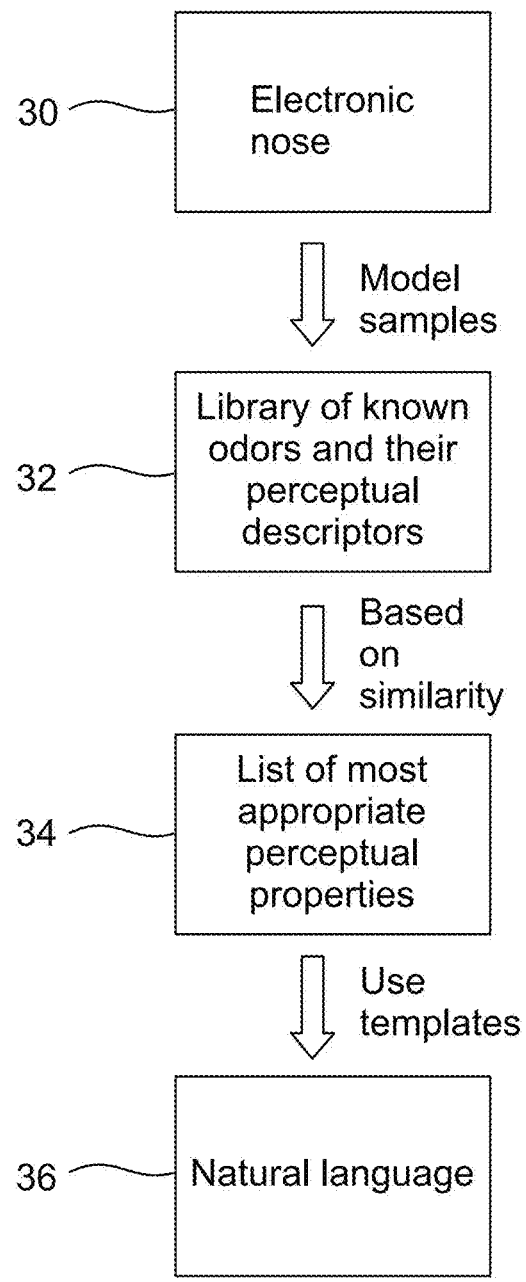

Reference is now made to FIG. 3, which is a simplified diagram that illustrates a three step process for providing the description. First, given a new sample, we analyze the sample in the enose 30, extract relevant enose features and calculate the perceived similarity of the sample to a library of known samples 32. Second, based on the similarity to the known library of samples we combine the perceptual qualities we know of the sample library and calculate the most appropriate perceptual qualities of the new sample 34. The third part of the process is to translate the list of perceptual descriptors found for our sample and express them in natural language —36. In the work that gave rise to the present embodiments, an AirSense PEN3 electronic nose as connected to an autosampler to sample odorants from glass vials.

An initial data set that was used to set up the sample space was provided from a collection of 77 single molecule samples drawn from the set used in Dravnieks' Atlas of Odor character profiles, and is referred to herein as Dataset A. [see supplementary material for the list of molecules] This set of mixtures was sampled in the enose at a flow rate of 350 ml/min through the electronic nose and the samples heated to 30 degrees Celsius by the autosampler. The 10 sensors of the enose sampled for 79 seconds so that for each sample the data collected consisted of 10 79-second time series. For each sample, we extracted 10 features, which were the sensor reading at the last time step. The reason is that at that point, the signal has stabilized and a sample at that point should provide the most robust features. All enose samples were diluted in propylene glycol and prepared inside specialized glass vials sealed by a silicone membrane.

As Dataset A consists of samples from the Dravnieks Atlas, we have for each samples a list of 146 perceptual descriptions and their level of applicability as rated in Dravnieks experiment.

The chemical properties of the molecules in Dataset A were obtained from a commercial software program called Dragon v6.

The natural language part of the project makes use of a collection of several hundred free text descriptors of odorant samples. The textual descriptions were collected by one of the present inventors for work on semantics of odorant descriptors, wherein test subjects were presented with odorants and asked to describe them using natural language. These texts are used as templates for the present process of generating natural language descriptions of odorants. The set of textual descriptions is labeled Dataset B.

The process of producing natural language descriptions involves the steps discussed above in respect of FIG. 3, which shows the process of producing natural language descriptions of olfactory samples.

The first stage of the process consists of modeling the perceptual distance of a tested sample to the library of known odor samples. Dataset A serves as the library of known odors and also the source of the test samples with each sample being modeled using the rest of the library (a leave one out process).

Each one of the 77 samples is sampled by the enose, and its enose features are used to calculate its perceptual distance from each of the samples in the library (in this case the remaining 76 samples). There are different ways in which the distance calculation can be performed however, the following steps do not depend on exactly which method is used to carry out this calculation. Our current method is to first map the enose features to a chemical space of selected Dragon chemical descriptors. Then using the chemical space representation of the test sample and of the library samples we calculate the perceptual similarity of the samples and the library samples. This process uses a specially optimized chemical space where the dimensions are chosen based on enose features, as discussed in greater detail hereinbelow. The set of n descriptors that best clusters the similar odors and keeps dissimilar odors far apart is selected.

The second part of the process consists of using the calculated similarities to the given library of odor samples and extracting from those the most appropriate perceptual descriptors of the test sample. To do that we take 15 library samples which are closest to the new sample. We weigh each of the 15 library odors sample by it distance to the test sample so that the closer the samples the higher the weight. We multiply the 15 library samples by their calculated weights and add them together. The resultant sum is a vector of perceptual properties reflecting the weights and the constituent 15 library samples. In this resulting vector, the size of the coefficient at a certain property reflects its relevance to the sample. To produce a compact perceptual description of the test sample we select the 5 properties where the coefficients of the calculated perceptual vector are largest. The end result is a list of 5 most appropriate perceptual properties, which are associated with the test sample.

To test the performance of our procedure we compared our selection of top 5 most relevant perceptual properties in the test sample with the actual ratings given by test subjects (in Dravniek's experiment). For each of the test samples, we checked the actual rank-order of the top 5 predicted perceptual properties. The results are depicted in FIG. 4, which graphs the results of predicting the top five verbal descriptors out of 146 for 77 molecules, and shows the rank order location of the top 5 predicted perceptual descriptors for odor samples in Dataset A.

Figure 4:
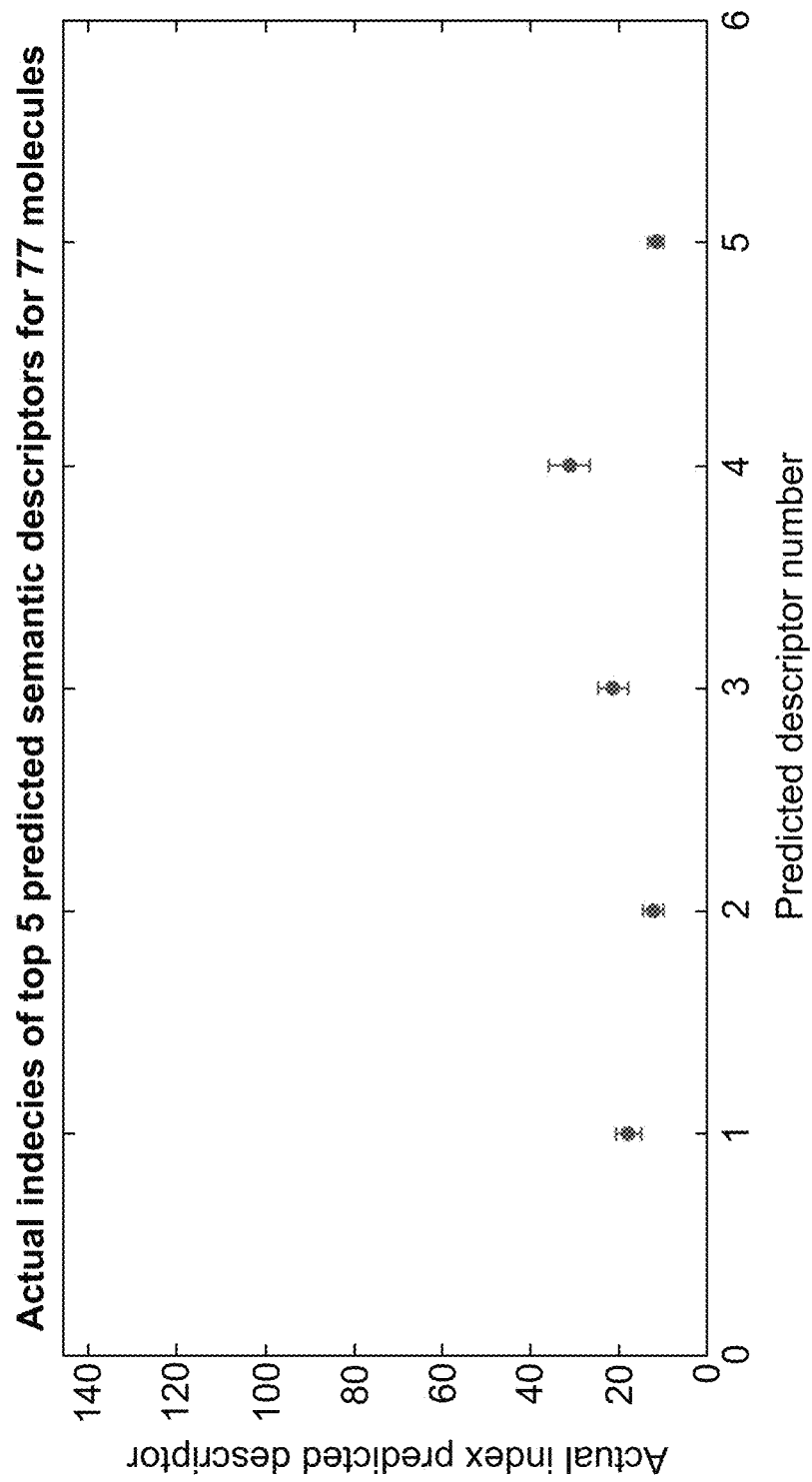

As can be seen in FIG. 4, the predicted top 5 descriptors are ranked near the top of the order of the actual rank-order of the descriptors. It was found that for 62 out of the 77 molecules we predicted at least one of the top 5 descriptors. The probability of obtaining such a result by chance is $p<e-50$. Moreover, for 47 out of the 77 molecules we predicted more than one of the top 5 descriptors, and for 30 out of the 77 molecules we hit the top descriptor. In general, across the 77 molecules the average ranking (out of a possible 146) of the 5 descriptors we predicted was 11. The probability of each of these results is $p<e-30$.

The third step in our process is to use the calculated top 5 descriptors to generate natural language descriptions of odorants. Since the text we need to generate is all about the same topic the simplest way to accomplish this is to use templates of actual descriptions given by test subjects. Such templates are generated from Dataset B—hereinbelow.

A difficult part of the present embodiments is the prediction of the perceptual distance between odorants sampled in the enose. However, as shown, the descriptor selection on the available data is highly accurate. Since the descriptor predictions are close to the actual ratings it is highly improbable that a person would be able to tell the top 5 descriptors we calculated from the real ones. In that sense, we can expect to pass an abstract version of the Turing test with the current algorithm. Once the top predictors are plugged into the templates (see supplementary material), the resulting descriptions may be even harder to distinguish from actual human descriptions.

Supplementary Information

1) The list of CID's of molecules included in Dataset A.

263
307
326
342
460
957
1049
1127
1140
1146
2758
3314
4133
5144
6054
6054
6184
6501
6544
6654
7059
7410
7519
7600
7685
7710
7714
7731
7749
7762
7770
7888
7921
7966
7991
8030
8103
8118
8129
8130
8148
8797
8892
8918
9609
10722
10821
10890
11002

11552
12178
14286
18827
19310
22201
22311
24915
26331
31252
31266
31276
31277
61016
61138
61199
62336
62433
62444
67285
91497
93009
439570
637563
638011
1550884
5281515
5283349

2) Sample of natural language templates. The banks are coded as ___ for an adjective and ___ for a noun.
I don't like this smell because it is too ___
To me, it smells like ___
This reminds me of ___
This is very ___
This reminds me of my childhood
This is very ___ it is like a ___
It is something ___
It smells a bit ___ sort of like a ___ or a ___
It is one of these ___ ___ smells
it's like a combination of ___ and ___
My dad used to have a ___ and it smelled like ___
When I close my eyes I see ___
This brings me back to my grandmother's house where she had ___ that smelled like this
I know what it is, it is ___
This has the aroma of a ___
A little ___ like a ___
I can't put my finger on it might be a ___
It reminds me of a ___ but more ___
It reminds me of a ___ I don't know why.
Call me crazy but I bet this is a ___
It is exactly like a ___ that you buy in the store
It's a ___ my mom used to bring me those
my older human brother once showed me a ___ that smelled like this
this is like a ___ but more synthetic
this is like a good version of a ___
a bit ___. smell of ___ ___ but ___.
this smells like ___, I like it.
this is like strong ___
this is like weak ___
this is very faint, a little ___
a smell which is ___ ___ ___
I don't recognize this, maybe a ___
it is something that I like, maybe ___
reminds me of ___
maybe ___
it's like a delicate version of a ___ really ___
hard to say, maybe like a ___
it took me a while to recognize it, I am pretty sure it is like ___
not exactly a ___ more like a ___ ___
almost like a ___
to me it smells really ___ and ___
I know I should recognize this, maybe ___
this is like something you smell in winter
It is on the tip of my tongue
It's like a mixture of ___ and ___
I know this but can' place it
I used to have it around my workplace
it is a bit ___ yet ___
it's like a ___ but more ___
it's like a ___ but less ___
it's the smell of ___ ___ ___ ___ like a ___
it's a ___ odor ___ reminds me of ___
I have a body cream which smells like this
it's a ___ but not so ___ relatively ___
maybe ___
is this a ___?
really ___
this smells exactly like a ___
a weird version of a ___
a bit ___ and ___
I date a guy once who smelled like this
I smell this on the number 17 bus
it's like a ___ mixed with a ___ ___
it is rot of like a ___ but not exactly
I know I smelled it before
personally, I hate it
I know some people might hate it but I like it
I would not want to wear this as perfume
too ___ to be a ___
I smelled this and immediately thought of ___

A second embodiment of the present invention relates to synthesizing the detected odor. We have developed a method for the synthesis of odorant mixtures which are intended to be indistinguishable from given odorant mixtures analyzed by an electronic nose. The present process starts from an unknown odorant mixture which we sample with an electronic nose. Secondly we model a chemical representation of the sample in a selected chemical space as discussed hereinbelow. Lastly, we use a large database of known molecules and their representation in our chemical space. We search this database and find a selection of molecules, which can be combined to produce a mixture with a chemical representation close enough to the sampled mixture as to be indistinguishable.

As in the previous embodiment, we use an AirSense PEN3 electronic nose connected to an autosampler to sample odorants from glass vials. Two sets of samples are involved. The first set is a collection of 86 single molecule and small mixture samples drawn from the set used in Dravnieks' Atlas of Odor character profiles referred to herein as Dataset B. [see supplementary material for the list of molecules] This set of mixtures was sampled in the enose at a flow rate of 350 ml/min through the electronic nose and the samples heated to 30 degrees Celsius by the autosampler. The 10 sensors of the enose sampled for 79 seconds so that for each sample the data collected consisted of 10 79-second time series. For each sample we extracted 10 features, which were the sensor reading at the last time step. The reason is that at that point the signal has stabilized and a sample at that point should provide the most robust features. All enose samples were diluted in propylene glycol and prepared inside specialized glass vials sealed by a silicone membrane.

The second set of samples consists of 14 mixtures of 4-10 molecules [see supplementary material for the list of molecules]. These mixtures were tested directly by test subjects who rated their perceived similarity, and are labeled Dataset C.

A third dataset used in this project is labeled Dataset D. It is similar in design to Dataset C except that it is made up of different choices of molecules and unlike the mixtures in Dataset C the components in these mixtures are of unequal intensities. The CID's of the components of the mixtures in Dataset C are listed in the supplementary material.

The chemical properties of the molecules we used were obtained from a commercial software program called Dragon v6.

Figure 5:
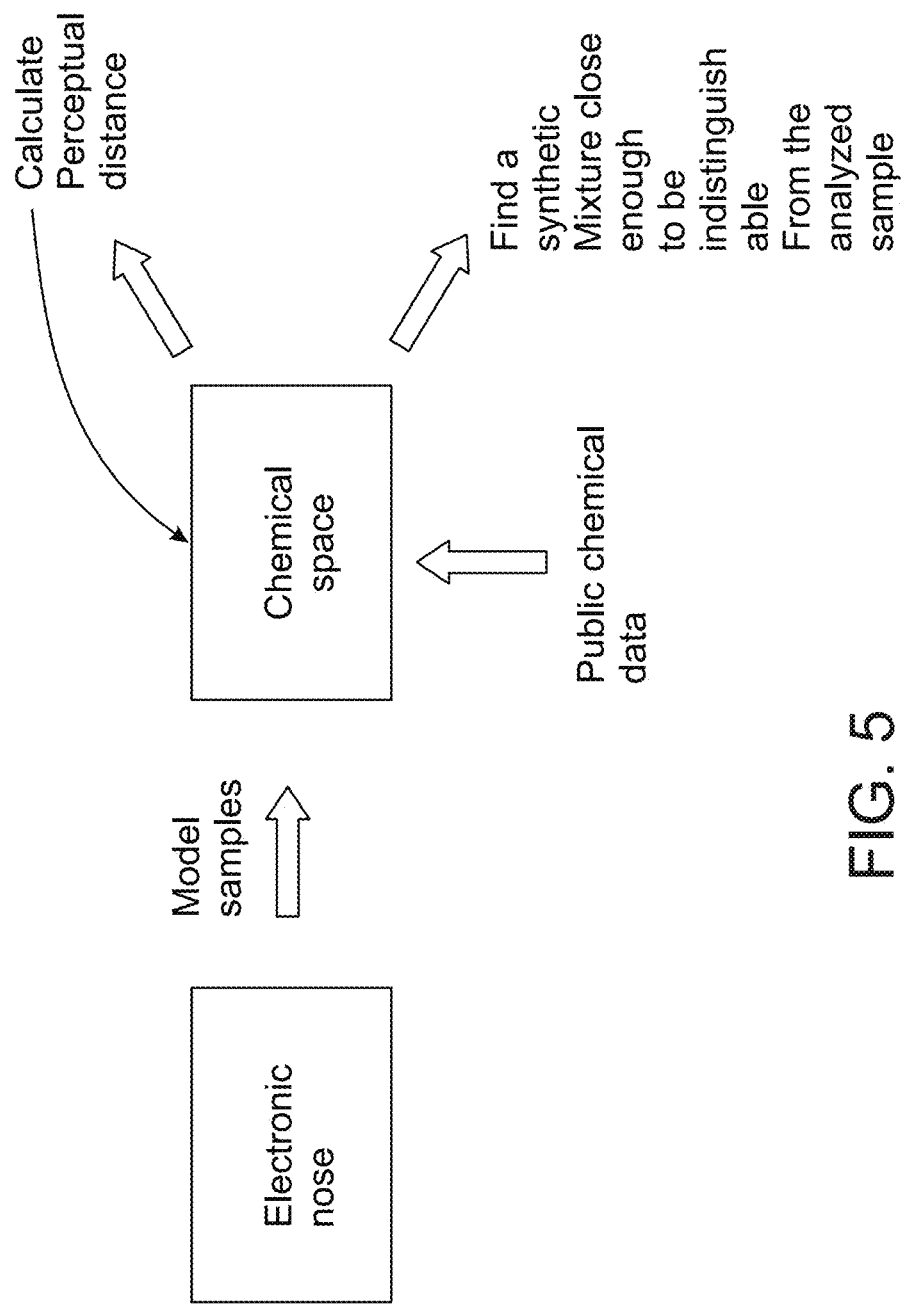

The process of calculating the synthetic mixture involves several steps illustrated in FIG. 5. FIG. 5 is a simplified flow chart illustrating the process of calculating a synthetic mixture. In earlier work we used a chemical space to represent odorants and model the perceptual distance from the chemical data. In this work, we want to use a similar step but we also want those chemical coordinates to be modeled by the enose features. To make that possible we find a specialized chemical space. This chemical space consists of those chemical properties, which are modeled well from the enose features.

Our starting point is a large list of all of the 4870 chemical properties produced by Dragon (excluding those, which were constant for all of our samples). Thus we had for each of our samples in dataset A a list of 4870 chemical properties. We then used a straightforward linear least square to try to model each of the chemical properties from the enose features. Only those of the chemical features which were significantly modeled below a threshold of ($p=0.01$) were retained for the second part of the modeling. This initial screening of chemical properties resulted in a set of 648 chemical properties, each one of which can be well modeled individually from enose features.

In the second stage of the modeling, we find a set of descriptors, which will predict the perceptual similarity of odorant mixtures. The modeling is restricted to those chemical properties, which are well modeled by the enose features. We used Dataset C to train and test this stage. First, we divided the set of comparisons between the mixtures in the dataset into a testing and a training set. The testing set consisted of 48 comparisons and the training set consisted of 47 comparisons. We tested 2000000 random selections of 18 chemical descriptors for their performance as a chemical space. That is for each of these 2000000 selections we created a chemical space with them as coordinates and calculated the angle distance between the comparisons in the training set. The selection, which performed best, is the one, which produced the best correlation of angle distance and actual subject-rated mixture similarity. The results were a set of 18 descriptors, which were then tested on the separate testing set of comparisons. The performance of the angle distance on the testing set was a correlation of ($r=-0.62$, $p=1.79$ e-6). To put this choice of descriptors to a harder test we used the mixtures in Database D, which have no common mixture with Database C on which the descriptors were selected. The test on Dataset D is also more difficult because unlike Dataset C the mixture components were not all of equal intensity so the testing is carried out on a different set of conditions. Nevertheless, the selection of 18 chemical descriptors performed very well in predicting the perceptual similarity of odorant mixtures in Dataset D.

Figure 6:
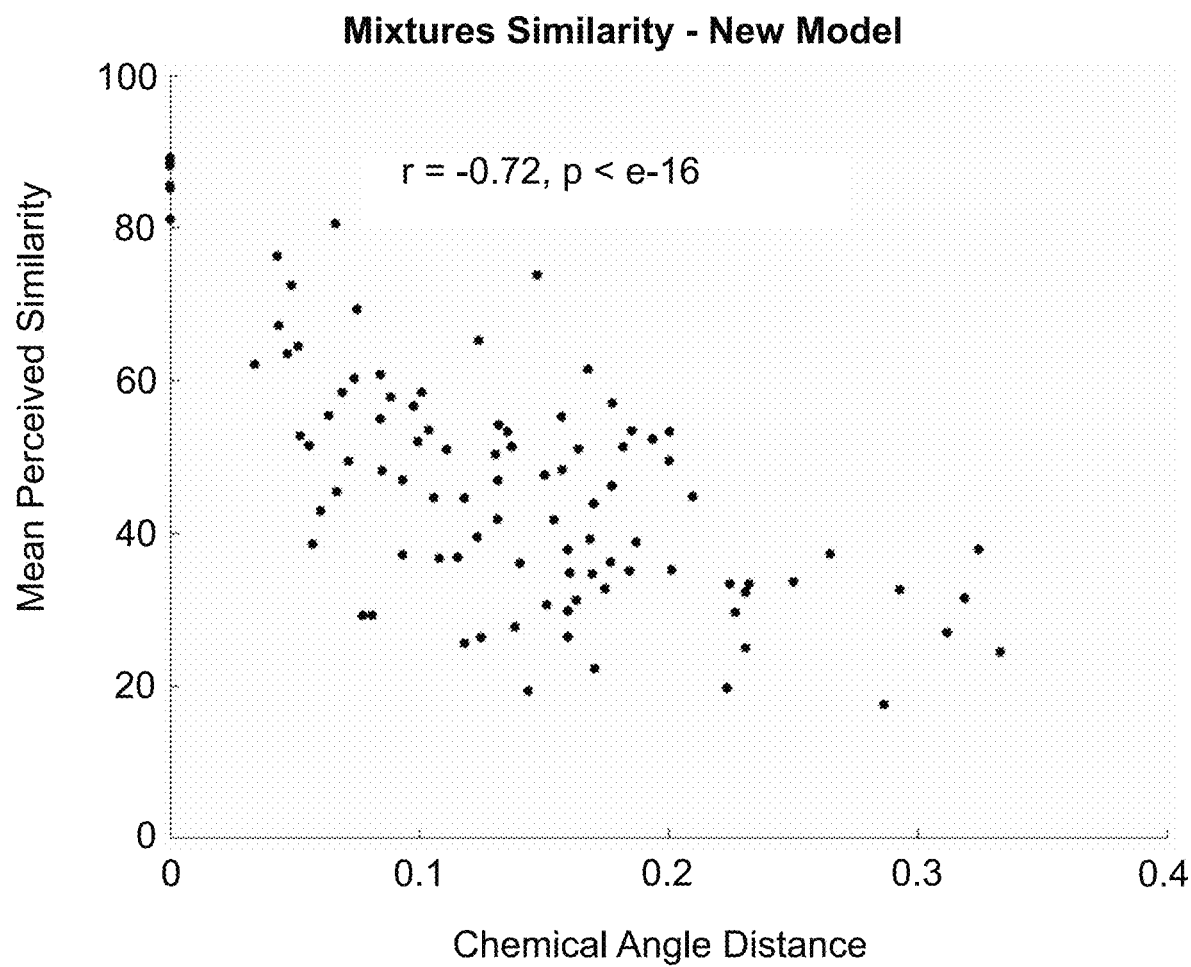

The results are depicted in FIG. 6. FIG. 6 shows the modeled perceptual similarity of all comparisons between 14 complex mixtures in Dataset D. $r=0.72$ ($p<10-16$) using 18 chemical properties which are also well modeled by enose features.

Having found a set of 18 well performing chemical descriptors, we fix those as the parameters in our chemical space (see supplementary material for a list of descriptors).

Figure 7:
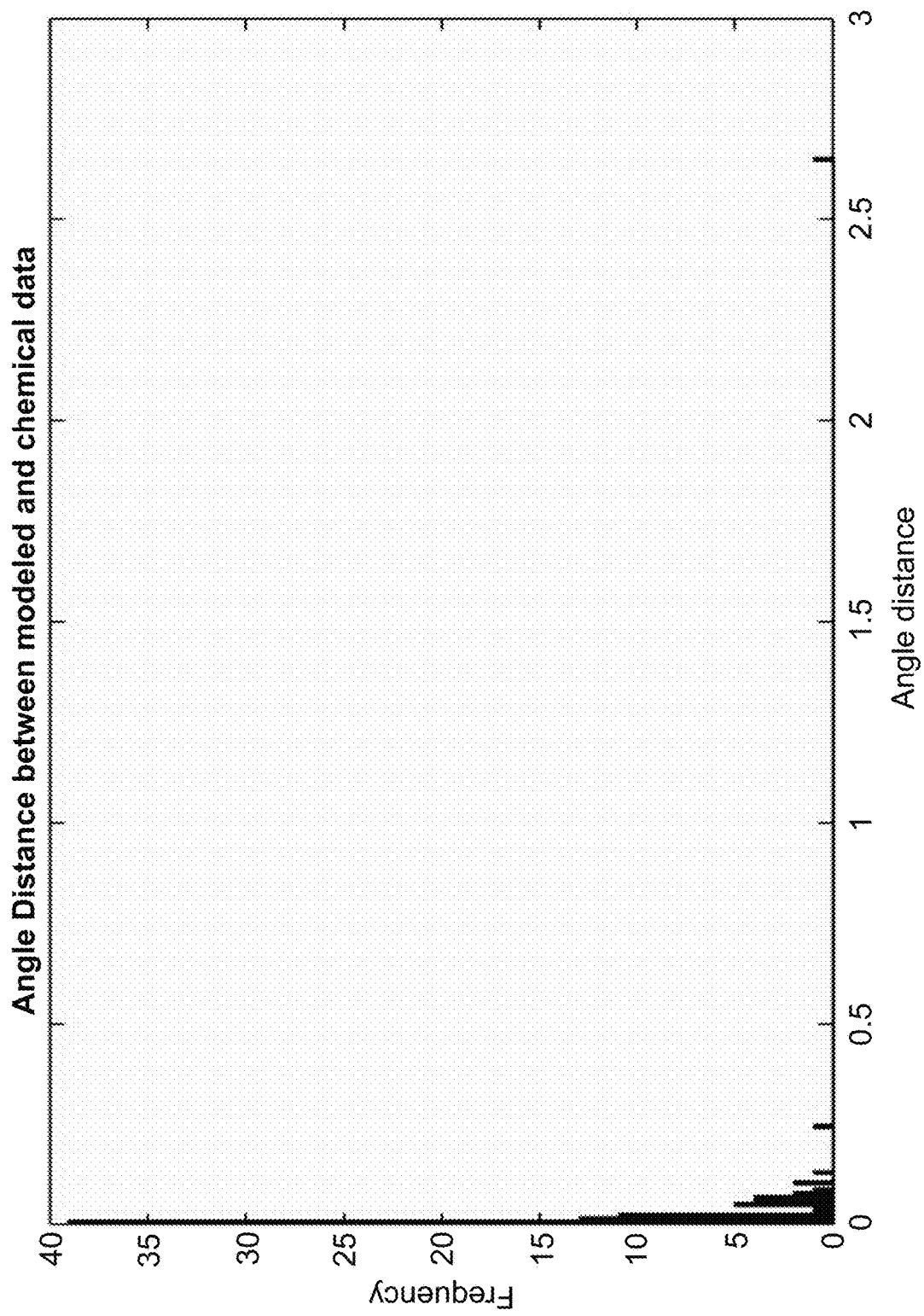

The next step in our effort is to see how well the representation of our mixtures in the chemical space we selected can be modeled from their enose features. The results are depicted in FIG. 7. FIG. 7 is a simplified diagram showing the angle distance between modeled and actual chemical representation in our optimized chemical space of 86 enose samples in Database B.

When observing FIG. 2 we can extrapolate that the just noticeable difference in odorant similarity corresponds to an angle distance lower than 0.033. The number of similarities, which we were able to predict to be closer than 0.033 to the original chemical representation is 63 out of 86 molecules, which is 73%. An additional 7 molecules are at right the level of just noticeable difference making a total of 81% at or below detectable difference.

What we can deduct from the data, which we have on hand, is two things. First, we are able to sample novel samples in the enose, extract from them relevant features and use these feature to model the representation of the samples in our chemical space. Second, we may use this chemical space to model perceived similarity of samples as rated by test subjects. Both these results are highly significant and should provide a solid basis for further testing.

The remaining part of the calculation is to calculate synthetic mixtures to approximate modeled samples. As illustrated in FIG. 5, given an unknown sample we can model it in our chemical spaces. Next, we use Dragon to produce a library of known components and their representations in our 18 dimensional chemical space. This part requires no further work other than the selection of molecules to include in our library. Using this library, we use linear algebra to find combinations of library vectors, which will combine to produce a vector approximating the chemical representation of our sample. The accuracy of the approximation can in practice be as high as we would like depending on how many components we would like to include in the synthetic mixture. Furthermore, one can add more preferences and restriction on the search for to obtain synthetic mixtures with desired properties. For example, one can restrict the search only to chemicals with an LD50 or price below a certain threshold.

Supplementary Material 1) list of CID's of 86 samples consisting of single Dravnikes molecules and small mixtures in Dataset B.

| | |
|---|---|
| mixture 1 | 91497 |
| mixture 2 | 12178 |
| mixture 3 | 263 |
| mixture 4 | 6184 |
| mixture 5 | 8118 |
| mixture 6 | 62336 |
| mixture 7 | 8103 |
| mixture 8 | 67285 |
| mixture 9 | 6054 |
| mixture 10 | 8129 |
| mixture 11 | 61016 |
| mixture 12 | 26331 |

-continued

| | | | | | |
|---|---|---|---|---|---|
| mixture 13 | 20859 | | | | |
| mixture 14 | 7770 | | | | |
| mixture 15 | 8103 | 91497 | | | |
| mixture 16 | 5144 | 6184 | | | |
| mixture 17 | 7888 | 7770 | | | |
| mixture 18 | 1127 | 7888 | | | |
| mixture 19 | 7762 | 3314 | | | |
| mixture 20 | 6054 | 7770 | | | |
| mixture 21 | 19310 | 8797 | | | |
| mixture 22 | 7762 | 62336 | 3314 | | |
| mixture 23 | 61016 | 4133 | 1049 | | |
| mixture 24 | 67285 | 8635 | 263 | | |
| mixture 25 | 62336 | 6054 | 460 | | |
| mixture 26 | 61016 | 62444 | 460 | | |
| mixture 27 | 8118 | 62444 | 7059 | | |
| mixture 28 | 263 | 1049 | 61016 | | |
| mixture 29 | 3314 | 67285 | 20859 | 8797 | |
| mixture 30 | 7762 | 8797 | 62336 | 3314 | |
| mixture 31 | 1550884 | 62336 | 8797 | 4133 | |
| mixture 32 | 20859 | 8130 | 3314 | 61016 | |
| mixture 33 | 7762 | 8797 | 8635 | 26331 | |
| mixture 34 | 1049 | 67285 | 62444 | 19310 | |
| mixture 35 | 26331 | 7762 | 8103 | 240 | |
| mixture 36 | 20859 | 7770 | 1550884 | 240 | 62433 |
| mixture 37 | 8118 | 1127 | 19310 | 6184 | 7059 |
| mixture 38 | 26331 | 7770 | 7519 | 19310 | 1550884 |
| mixture 39 | 3314 | 1049 | 61016 | 7059 | 1550884 |
| mixture 40 | 61016 | 8129 | 7762 | 3314 | 8635 |
| mixture 41 | 61016 | 19310 | 1550884 | 8129 | 3314 |
| mixture 42 | 8129 | 22201 | 7685 | 7888 | 8635 |
| mixture 43 | 61199 | | | | |
| mixture 44 | 7410 | | | | |
| mixture 45 | 14286 | | | | |
| mixture 46 | 98403 | | | | |
| mixture 47 | 6501 | | | | |
| mixture 48 | 7710 | | | | |
| mixture 49 | 31266 | | | | |
| mixture 50 | 31276 | | | | |
| mixture 51 | 10890 | | | | |

-continued

| | |
|---|---|
| mixture 52 | 7600 |
| mixture 53 | 62433 |
| mixture 54 | 637563 |
| mixture 55 | 7519 |
| mixture 56 | 240 |
| mixture 57 | 93009 |
| mixture 58 | 263 |
| mixture 59 | 11002 |
| mixture 60 | 439570 |
| mixture 61 | 5281515 |
| mixture 62 | 307 |
| mixture 63 | 638011 |
| mixture 64 | 342 |
| mixture 65 | 8797 |
| mixture 66 | 7685 |
| mixture 67 | 7731 |
| mixture 68 | 326 |
| mixture 69 | 7966 |
| mixture 70 | 8148 |
| mixture 71 | 9609 |
| mixture 72 | 24915 |
| mixture 73 | 22201 |
| mixture 74 | 31252 |
| mixture 75 | 12265 |
| mixture 76 | 19310 |
| mixture 77 | 7762 |
| mixture 78 | 7749 |
| mixture 79 | 26331 |
| mixture 80 | 2758 |
| mixture 81 | 3314 |
| mixture 82 | 460 |
| mixture 83 | 8130 |
| mixture 84 | 8129 |
| mixture 85 | 6184 |
| mixture 86 | 8892 |

2) list of CID's of molecules used in the 14 mixtures in Dataset C.

| | | | | | | | | | |
|---|---|---|---|---|---|---|---|---|---|
| mixture 1: | 326 | 26331 | 1140 | 6544 | | | | | |
| mixture 2: | 7410 | 240 | 93009 | 8635 | | | | | |
| mixture 3: | 7710 | 62433 | 7519 | 7685 | 3314 | | | | |
| mixture 4: | 31276 | 8148 | 7762 | 18827 | 7714 | | | | |
| mixture 5: | 7519 | 8148 | 31252 | 8103 | 5281168 | 6544 | | | |
| mixture 6: | 7410 | 326 | 2758 | 62444 | 7770 | 1140 | | | |
| mixture 7: | 240 | 307 | 7731 | 2758 | 12178 | 62336 | 8635 | | |
| mixture 8: | 31276 | 62433 | 8129 | 12178 | 7519 | 18827 | 10722 | | |
| mixture 9: | 7710 | 93009 | 8130 | 8103 | 5281168 | 7059 | 8918 | 7714 | |
| mixture 10: | 7410 | 11002 | 8797 | 7519 | 8129 | 5281168 | 6654 | 8030 | |
| mixture 11: | 62433 | 8797 | 2758 | 3314 | 8635 | 61138 | 6544 | 6054 | 10722 |
| mixture 12: | 11002 | 307 | 7685 | 12178 | 4133 | 7991 | 6054 | 7770 | 7714 |
| mixture 13: | 8797 | 7731 | 7966 | 3314 | 62336 | 7059 | 7991 | 61138 | 6054 | 6544 |
| mixture 14: | 240 | 2758 | 8130 | 8129 | 5281168 | 7059 | 4133 | 8918 | 957 | 6654 |

3) list of CID's of molecules used in the 14 mixtures in Dataset C.

| | | | | | | | | | |
|---|---|---|---|---|---|---|---|---|---|
| mixture 1: | 520296 | 9012 | 24834 | 8180 | | | | | |
| mixture 2: | 62351 | 5367698 | 6050 | 7765 | | | | | |
| mixture 3: | 5365049 | 14104 | 170833 | 1550470 | 31219 | | | | |
| mixture 4: | 11086 | 17121 | 8180 | 61670 | 7194 | | | | |
| mixture 5: | 170833 | 17121 | 2214 | 6560 | 10925 | 23642 | | | |
| mixture 6: | 126 | 520296 | 5273467 | 6997 | 7657 | 24834 | | | |
| mixture 7: | 9012 | 556940 | 61670 | 5273467 | 61331 | 7601 | 7765 | | |
| mixture 8: | 11086 | 14104 | 807 | 61331 | 170833 | 18554 | 31219 | | |
| mixture 9: | 5365049 | 6050 | 11980 | 6560 | 10925 | 325 | 8077 | 7194 | |
| mixture 10: | 62351 | 5364231 | 7593 | 444972 | 807 | 10925 | 565690 | 126 | |
| mixture 11: | 14104 | 7593 | 2214 | 6998 | 7765 | 89440 | 23642 | 637776 | 31219 |
| mixture 12: | 5364231 | 556940 | 1550470 | 61771 | 778574 | 61293 | 637776 | 7657 | 7194 |
| mixture 13: | 7593 | 61670 | 61771 | 6998 | 7601 | 325 | 61293 | 89440 | 637776 | 23642 |
| mixture 14: | 5367698 | 5273467 | 11980 | 807 | 6997 | 325 | 778574 | 8077 | 444972 | 565690 |

4) list of 18 chemical descriptors used to define our current chemical space.

'P_VSA_e_5': P_VSA-like on Sanderson electronegativity, bin 5

'Eig05_EA(ed)': eigenvalue n. 5 from edge adjacency mat. weighted by edge degree 'Mor15e': signal 15/weighted by Sanderson electronegativity 'MATS7i': Moran autocorrelation of lag 7 weighted by ionization potential 'L3u': 3rd component size directional WHIM index/unweighted 'Eig02_EA(ed)': eigenvalue n. 2 from edge adjacency mat. weighted by edge degree 'Ho_G': Hosoya-like index (log function) from geometrical matrix 'SpAbs_B(p)': graph energy from Burden matrix weighted by polarizability 'SpAD_EA(bo)': spectral absolute deviation from edge adjacency mat. weighted by bond order 'VR1_B(m)': Randic-like eigenvector-based index from Burden matrix weighted by mass 'WiA_RG': average Wiener-like index from reciprocal squared geometrical matrix 'CID': Randic ID number 'Mor24m': signal 24/weighted by mass 'H0e': H autocorrelation of lag 0/weighted by Sanderson electronegativity 'SP01': shape profile no. 1

'Eta_betaS': eta sigma VEM count

'Mor01s': signal 01/weighted by I-state

'R2v': R autocorrelation of lag 2/weighted by van der Waals volume.

As per the above, a method of characterizing and distinguishing different smells is provided, based on measurement. In the following embodiment, a measure of smell is used to define the just noticeable difference (JND) for the sense of smell. Based on the JND, a digital system for reproducible measurement of smells may be provided.

The Just Noticeable Difference (JND) informs us of the minimal requirements for sensors and circuits in a sensory system, and thus shapes experiments probing the sensory neurobiology of vision and audition. These JNDs are for example critical for the design of digitizing devices such as televisions and telephones. The color and tonal JNDs were identified by testing discriminability of stimuli systematically varying along the physical measures of wavelength and frequency respectively, but what physical measure can we vary for odor quality? The lack of such a measure has posed a major hindrance for olfaction science, as aptly captured in a challenge posed ~100 years ago by none other than Alexander Graham Bell:

"Can you measure the difference between one kind of smell and another? It is very obvious that we have very many different kinds of smells, all the way from the odor of violets and roses up to asafoetida. But until you can measure their likenesses and differences you can have no science of odor".

Consistent with this statement, in order to define an olfactory quality JND, it is necessary that we have in hand a measure of smell by which to vary odor stimuli. One can base such a measure on any of the several largely converging models of olfactory perceptual quality space have been put forth over the last decade, an example of which is described hereinabove. The most basic models typically rely on finding mathematical rules that link odorant structure to odor perception. Odorant structure is typically derived from large numbers of physicochemical descriptors applied to molecules. These physicochemical descriptors are almost always obtained using Dragon software, and odor perception is typically derived from large numbers of verbal descriptors applied to odorants. The simpler models successfully use odorant structure alone to predict primary perceptual axes of smell, to predict perceptual phenomena such as olfactory white, to predict individual odorant descriptors, and indeed provide for a metric that links odorant perceptual similarity to odorant structure. Although this model has brought us closer to meeting Bell's challenge, it is to date limited in that it applied only to lab odorants whose molecular components have been equated for perceived intensity. Real-world odorants such as Bell's rose, violet and asafoetida are very different from lab odorants in that they are made of many components with vastly differing intensities. If one wants to uncover the olfactory JND, one must first overcome this limitation. To this end, we first set out to generate a similarity algorithm applicable to real-world odorants with varying intensity components. Once we achieved this, we used this novel measure to identify the smallest difference in odor quality that humans can detect, or the odor quality JND.

A Measure of Smell Predicts Real-World Odorant Perceptual Similarity from Odorant Structure Alone We selected 44 monomolecules as detailed in Supplementary Data 1. These molecules provide an effective span of physicochemical (FIG. 8A) and perceptual (FIGS. 12A, B) olfactory space. In Experiment 1, we asked 23 participants (16 women, age 27.7±3.3) to rate the perceived intensity of each monomolecule alone. After observing that we have in hand monomolecules widely ranging in perceived intensity (FIG. 8B), we then used these molecules to generate 14 varying-intensity complex mixtures ranging in component number between 4 and 10. In Experiment 1b we then asked participants to rate all pairwise perceptual similarities between all 14 mixtures (i.e., similarity of mixture #1 to mixture #2, similarity of mixture #1 to mixture #3, and so on, including four instances of comparing each odorant mixture to itself), culminating in 95 pairwise mixture similarity ratings (All similarity ratings in this manuscript are detailed in Supplementary Data 2).

Figure 8A:
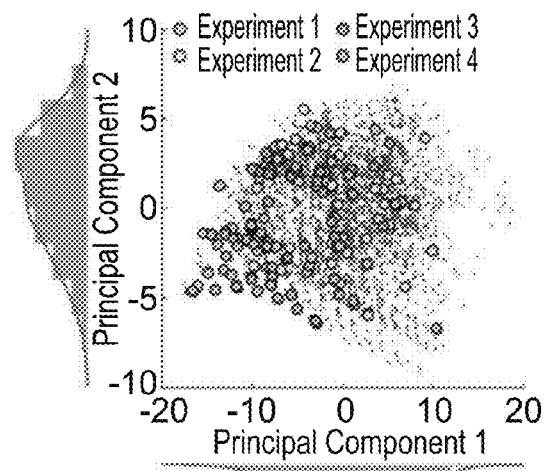
Figure 8B:
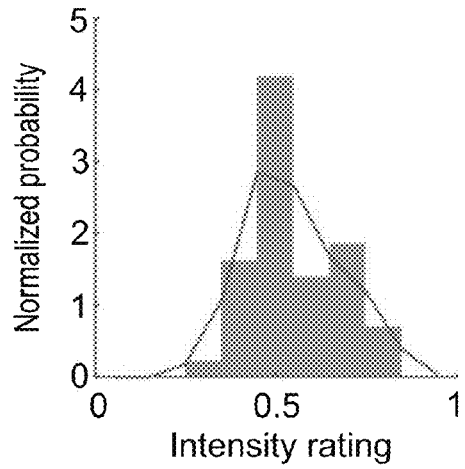
Figure 8C:
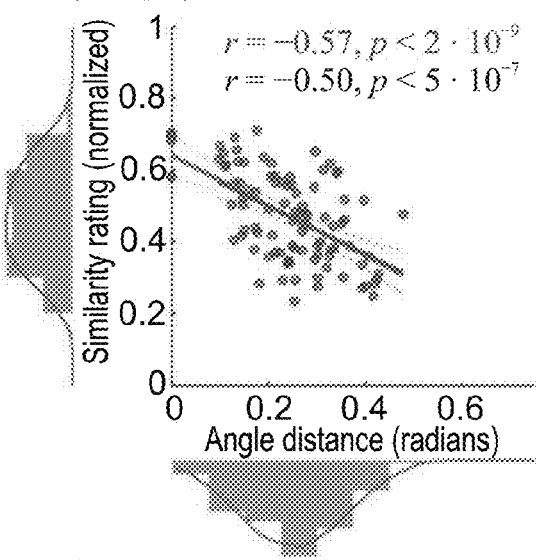
Figure 8D:
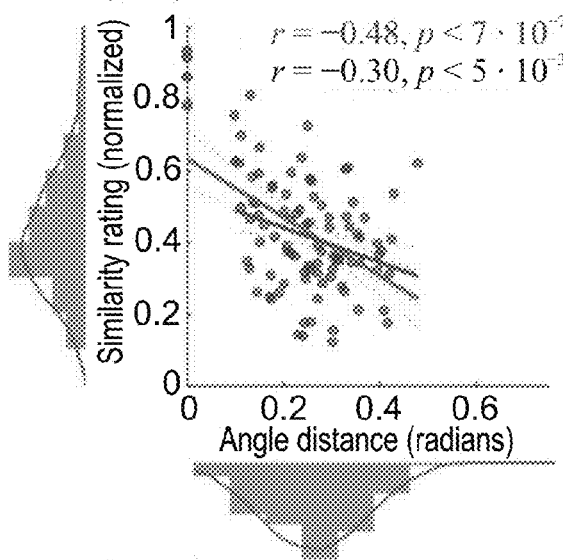
Figure 8E:
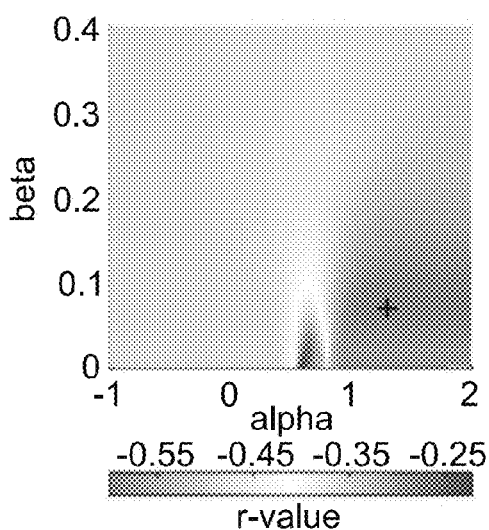
Figure 8F:
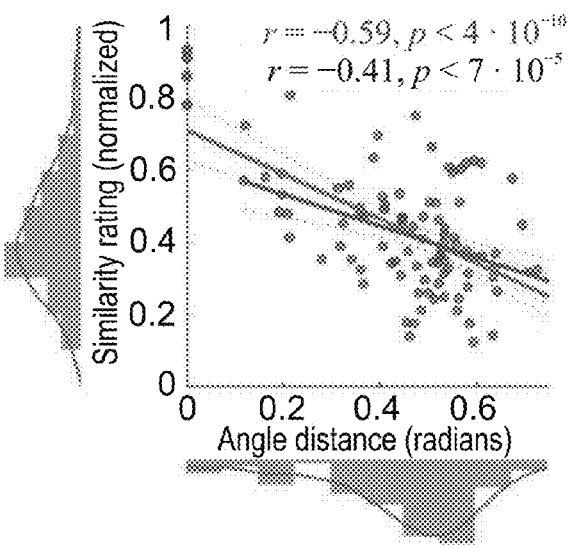

Referring now to FIG. 8A, the 148 molecules used across experiments are overlaid on 4046 molecules within the first and second Principal Components of a physicochemical space. FIG. 8B is a histogram of intensity ratings provided by 22 participants for 44 odorants used in Experiment 1. FIG. 8C to FIG. 8F are scatter plots where each dot is a pairwise comparison of two odorants, on the Y axis their actual similarity as rated by participants (n=22, two repetitions each) is given, and on the X axis their distance is shown according to the model being tested. FIG. 8C shows original similarity model applied to odorants first equated for perceived intensity. FIG. 8D shows the original similarity model applied to Experiment 1 results with odorants of varying intensities. FIG. 8E shows variation in correlation between predicted and actual perceptual similarity as a function of variation in $\alpha$ and $\beta$. The point of optimal performance is denoted by a black cross. FIG. 8F shows a novel similarity model applied to Experiment 1, which results in odorants of varying intensities. Red lines through data are linear fits.

We calculate the difference between mixtures as done previously: In brief, the distance function between the vector representing mixture u and the vector representing mixture v was computed as the angle between them in a 21 physicochemical descriptor space (Supplementary Table 1). The angle is given by $$\theta(\vec{u}, \vec{v}) = \arccos\left(\frac{\vec{u} \cdot \vec{v}}{|\vec{u}| \cdot |\vec{v}|}\right)$$

where $\vec{U} \cdot \vec{V}$ is the dot product between the vectors and $|\vec{u}|$ and $|\vec{v}|$ are their Euclidean norms.

When using the same mixtures after first individually diluting each of their components to equal perceived intensity (i.e., lab mixtures), the previous similarity model provides for a correlation of $r=-0.57$, $p<2\cdot10^{-9}$ between predicted, from structure, and actual perceptual similarity of lab mixtures (FIG. 8C, red line). However, when we apply this previous model to estimates made on the current mixtures containing the same components but varying in intensity (i.e., real world mixtures), the correlation drops from $r=-0.57$ to $r=-0.48$, $p<7\cdot10^{-7}$ (FIG. 8D, red line). Notably, there are two ways to calculate and plot such overall correlations between predicted and actual odorant similarity: either with or without comparisons between identical mixtures (there are arguments for each approach, see Methods). The above is with such comparisons, but had we removed them, the correlation shifts from $r=-0.50$, $5\cdot10^{-7}$ using equated-intensity lab mixtures (FIG. 8C, black line) to $r=-0.30$, $p=0.005$ using varying-intensity real world mixtures (FIG. 8D, black line). In other words, the impact of intensity on model performance may be even greater.

In order to recover model performance so as to apply to real-world mixtures, we developed and applied a universal intensity factor. This factor adjusted the weight of each component in a mixture to reflect its perceived intensity in an exponential way (see Methods). In brief: A sigmoidal function model was fitted in order to describe the nonlinear nature of the weightings of the vectors in the mixture. We set out to identify the universal parameters that best fit any monomolecule's perceived intensity to its vector length in the mixture model. Or in other words, we sought the parameters that optimize the correlation between actual similarity ratings and weighted angle distance for Experiment 1 results. We systematically varied $\alpha$ and $\beta$ in the equation $$w(x) -= \frac{1}{\lambda + e^{-\frac{x-\alpha}{\beta}}}$$

in order to incorporate component intensity in vector length. We then recalculated the correlation between weighted angle distance and perceived similarity for each parameter set ($\alpha$ and $\beta$). We selected the pair of parameters that resulted in the best correlation (largest negative value). We found that these universal parameters were $\alpha=-1.3$, $\beta=0.07$ (FIG. 8E), which results in the following $$w(x) = \frac{1}{1 + e^{-\frac{x-1.3}{0.07}}},$$

where x represents the normalized intensity.

Using this weighting in the model recovered its performance from $r=-0.48$ to $r=-0.59$, $p<3\cdot10^{-10}$ between predicted (from structure) and actual real-world mixture perceptual similarity (FIG. 8F, red line), bringing it to a performance level equal to that of the previous model when applied to intensity-equated mixtures (Z (two-tailed)=0.20, p=0.84). This reflects a 23% improvement in correlation, or a 51% increase in explained variance (R2 statistic) by the new model compared to the old model when using varying intensity real world mixtures. Note that again, if we disregard pairwise comparisons of identical mixtures, the improvement provided by the new model is even greater, from $r=-0.30$ p=0.005 (FIG. 8D, black line) to $r=-0.41$, $7\cdot10^{-5}$ (FIG. 8F, black line), or a 36% improvement in prediction, and a 86% increase in explained variance.

Because we tested the model using the same data from which it was developed, we next set out to verify the generalization of this new model to novel data. In Experiment 2, we replicated procedures of Experiment 1, yet using 14 new mixtures from a set of 44 new monomolecules we had never used before (FIG. 8A, FIG. 12A, FIG. 12B). Here, the original lab-odor similarity model is provided for a prediction of perceptual similarity from structure alone at $r=-0.58$ ($p=7\cdot10^{-10}$) (FIG. 9B, red line), yet the new weighted real-world similarity model provided for an even stronger and remarkable correlation of $r=-0.76$, $p<5\cdot10^{-19}$ between predicted from structure and actual perceptual similarity (FIG. 9C, red line). This is a significant improvement (Z (two tailed)=2.26, p=0.024), that reflects a 31% improvement in correlation, or a 70% improvement in explained variance. Moreover, again, the improvement provided by the new model is even greater when removing comparisons of identical mixtures, from $r=-0.38$, $3\cdot10^4$ using the old model (FIG. 9B, black line) to $r=-0.69$, $p<4\cdot10^{-14}$ using the new model (FIG. 9C, black line). This reflects an overwhelming 82% improvement in correlation, and a 330% increase in explained variance by the new model.

Figure 9A:
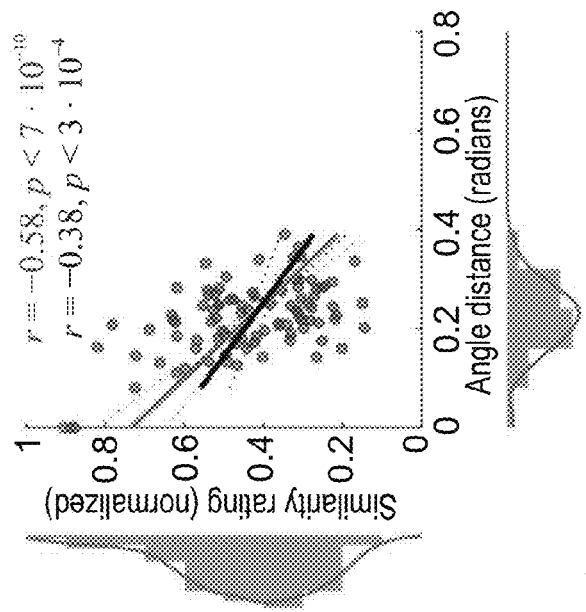
Figure 9B:
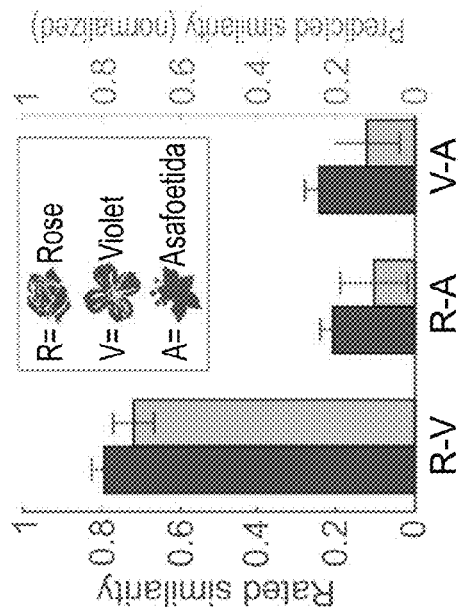
Figure 9C:
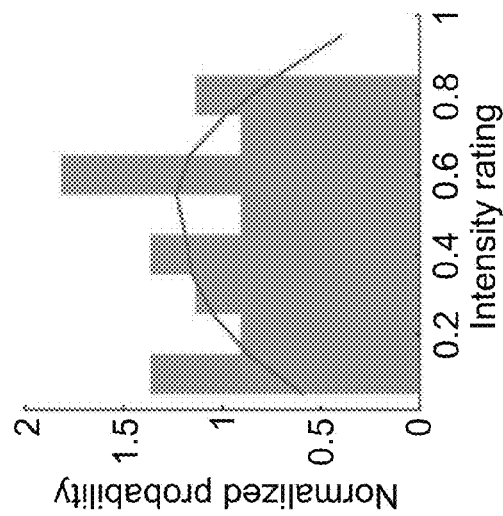
Figure 9D:
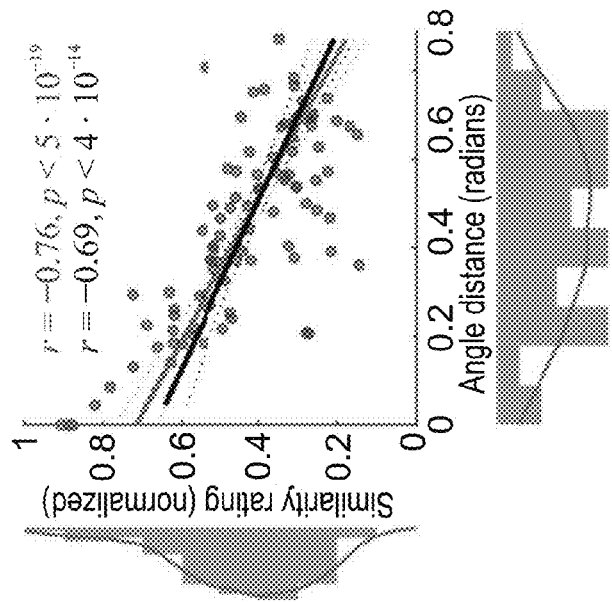

Reference is now to FIGS. 9A-9D, which is a series of graphs showing how the measure of smell predicts the perceived similarity of rose, violets, and asafoetida. More particularly, FIG. 9A is a histogram of intensity ratings provided by 30 participants for 43 odorants (three repetitions each) used in Experiment 2. FIGS. 9B-C are scatter plots where each dot is a pairwise comparison of two odorants showing, on the Y axis their actual similarity as rated by participants (n=31, 2 repetitions each), and on the X axis their distance according to the model being tested, FIG. 9B is the original similarity model applied to Experiment 2 results with odorants of varying intensities, and FIG. 9C is a novel similarity model applied to Experiment 2 results with odorants of varying intensities. FIG. 9D illustrates solving Bell's challenge: Predicted (light blue) versus actual (dark blue) pairwise similarity of Rose, Violet, and Asafoetida in Experiment 3 (n=30, 2 repetitions each). In other words, the parameters identified in Experiment 1 were generalizable to novel data that was not part of the building set, where they now provide improved predictions. This is a pleasant surprise given that predictive models typically perform worse, not better, when using novel data. We speculate that the differences in gained performance provided by the intensity factor across experiments reflect the molecule-specific concentration-to-perceived-intensity curves. If a mixture is made of components that have steep concentration-to-intensity curves, the impact of the factor will be large. If a mixture is made of components that have shallow concentration-to-intensity curves, the impact of the factor will be smaller.

We now have in hand a model that allows us to predict the perceptual similarity of real-world odorant mixtures containing components ranging in their perceived intensity, and this from their molecular structure and component intensity ratings alone. With this, we set out to ask whether we can finally meet Bells' challenge. A Master Perfumer provided us with detailed recipes for rose, violet and asafoetida, containing 10-11 components each (Supplementary Table 2). In Experiment 3, we first had participants rate the perceived intensity of each component. We then used our model to predict the perceptual similarity ("likenesses and differences" in Bells' language) of these mixtures based on their structure and component intensity alone. Finally, 31 different participants smelled the mixtures and rated their actual perceptual similarity. We observed a remarkable fit between predicted and actual similarity. We converted angle distance to normalized predicted similarity on a scale ranging from 0 to 1, according to the results of Experiments 1 and 2 (see Supplementary FIG. 2):

Violet/Rose predicted=0.72±0.06, observed=0.79±0.18, t=−0.41, p=0.68,
Rose/Asafoetida predicted=0.10±0.13, observed=0.21±0.17, t=−0.59, p=0.56,
Violet/Asafoetida predicted=0.12±0.13, observed=0.24±0.20, t=−0.58, p=0.57) (FIG. 9D), or in other words, we submit that we have met Bells' 104-year-old challenge. A web-based prototype is provided in accordance with the present embodiments that allows the user to easily implement these algorithms and calculate the perceptual similarity or difference between any two odorant mixtures. The user can select between testing pre-built mixtures (e.g., rose, violet and asafoetida), or building their own mixtures using a combination of any number of molecules from a building set of ~4,000 molecules.

The Measure of Smell Predicts Performance at Odorant Discrimination

Because odors that are more similar to each other are harder to discriminate, a measure that predicts similarity should also predict performance in a discrimination task. A standard discrimination task is the triangle test where participants are provided with three odorant samples, two of them identical, and one different. Their task is to identify the odd odorant. We applied our measure to the Bushdid dataset, a large set of triangle experiments conducted in 26 participants who performed 260 triangle decisions on mixtures ranging in component number from 10 to 30. We observed a correlation of r=0.56 (p<5E-23) between the predicted similarity of the mixtures according to our metric and participant's ability to discriminate them. Moreover, we observed that the more components in the mixture, the better our metric performed, culminating at r=0.68 (p=3E-12) for the 30 component mixtures (FIG. 9A). Because 30 component mixtures are more similar to real world odors than 10 component mixtures, we consider the latter value a more realistic reflection of performance.

Figure 10B:
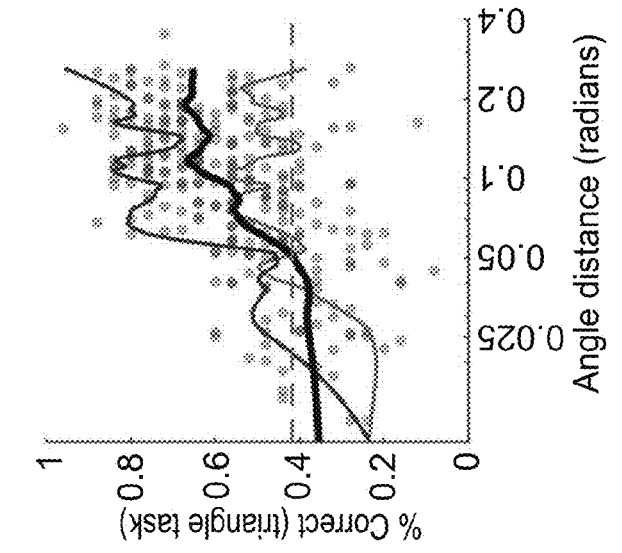
Figure 10A:
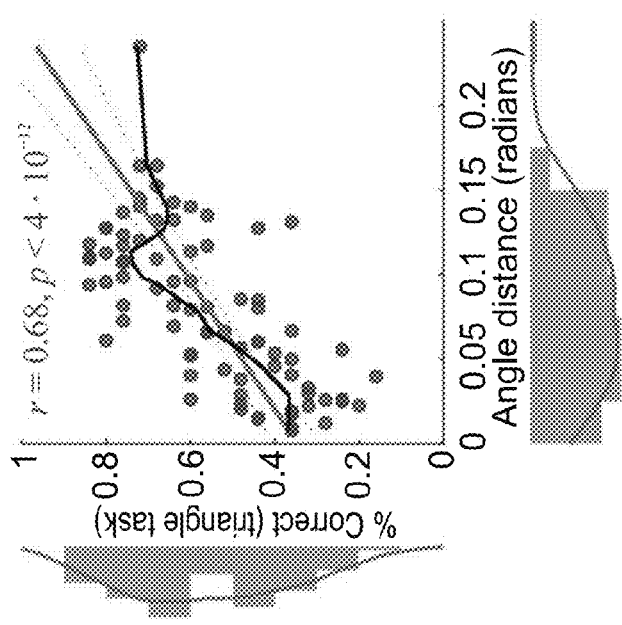
Figure 10C:
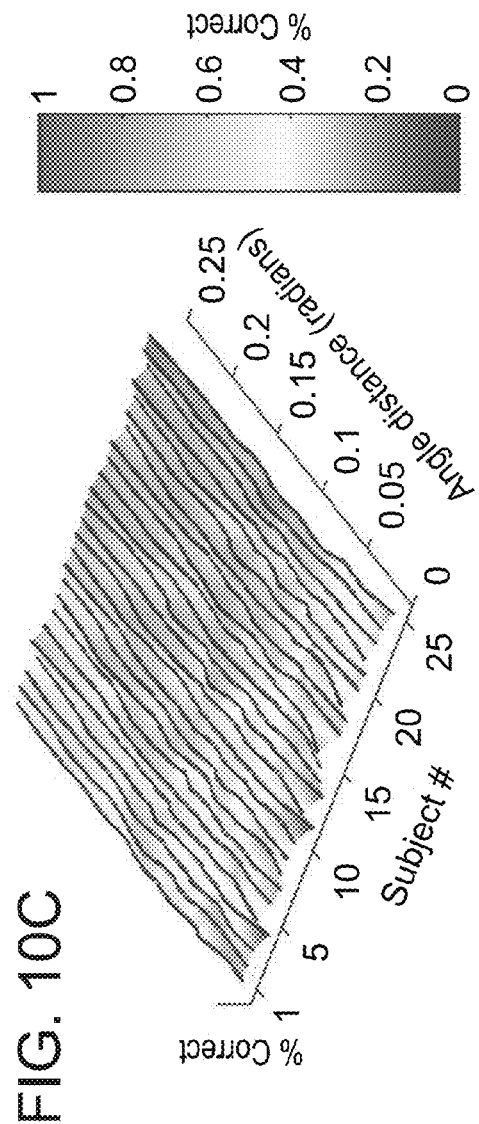

Reference is now made to FIGS. 10A-10C, which show how a measure of smell predicts performance in olfactory discrimination tasks. FIGS. 10A and 10B are scatter plots where each dot is a triangle test performed by 26 participants. On the Y axis is % accuracy, and on the X axis is the distance between the odorants according to our model. FIG. 10A shows performance in the triangle task as a function of angle distance using 30-component mixtures. The red line is a linear fit; the black line is a moving average. FIG. 10B shows performance in the triangle task as a function of angle distance using all data. The thick black line is the moving average, the thin dark blue line is the best performer, and the thin light blue line is the worst performer. The dashed red line indicates 41.8% accuracy, or d'=1.

FIG. 10C shows performance displayed by individual participant rather than by odorant comparison, sorted by performance. Z-axis and color both code subject performance accuracy. 41.8% accuracy, or d'=1, are color coded in white, red is d'<1, blue is d'>1.

The Measure of Smell Uncovers the Just Noticeable Difference (JND) in Odor Quality Given that, our measure is clearly associated with discriminability (FIG. 9A), we can now ask what is the value in our measure that is associated with the tipping point in the task, namely the smallest distance between odors where people first reliably discriminate between them. This value is in fact the Just Noticeable Difference (JND) in olfactory quality. In olfaction, there are JNDs in odor intensity, but no framework for JND in odor quality. Thus, we set out to identify the JND in the Bushdid data, concentrating on the more realistic 30 component mixtures. We also replicated all analyses using all mixtures rather than only 30 component mixtures, and this does not generate a major shift in results.

The JND is typically attributed to a d-prime (d') score of "1". In the triangle test, d'=1 is at 41.8% accuracy. We observe that in the Bushdid data, 41.8% accuracy was obtained at an angle distance of 0.051 radians between odorants (FIG. 9B). In other words, the Bushdid triangle data implied that the JND in olfactory quality space is 0.051 radians. To get a sense of the possible variance in this value we look at the top 5% of performers and bottom 5% of performers, which in this data reflect the very best and very worst performer. We observe that the best performer had a JND of 0.02 radians (FIG. 10B) and the worst performer had a JND of 0.14 radians (FIG. 10B). This is in fact the second worst, as the worst was anosmic. Between these two extremes, we can observe a relatively stable JND across participants (FIG. 10C). Thus, we conclude that the JND for this triangle data ranges between a minimum of 0.02 and maximum of 0.14, and its average is 0.051 radians.

In order to reduce the variability in this JND estimate we sought to increase our resolution. A strength of the Bushdid data is the range of possible JNDs that it spans. Its ensuing weakness is its lack of relative power at a given JND. With this in mind we set out to test additional individuals, with a larger number of subjects at each given angle distance. For Experiment 4 we designed and generated 100 new odor mixtures selected to provide for 50 pairwise comparisons, 10 at each of the following angle distances:

0.0125, 0.025, 0.05, 0.2, and 0.4 radians.

These distances were selected because they are in the vicinity of our initial estimate of the human olfactory JND. We then tested ~27 participants (27±10.4) on each comparison twice, providing for a total of 2,720 triangle decisions. All the discrimination results in this manuscript are detailed in Supplementary Data 3. We observed a clear psychometric relationship between log-angle-distance and triangle performance, with 41.8% accuracy falling just under 0.025 radians (FIG. 10C).

In other words, our triangle results were highly similar to the Bushdid triangle results, when compared in terms of performance as a function of angle distance between mixtures. In these experiments, we shift to reporting and plotting in log scale because the stimuli were designed along a log scale of angle distance.

Referring now to FIGS. 11A and 11B, we see scatter plots where each dot is a triangle test performed by a group of participants. On the Y axis is % accuracy, and on the X axis is the distance between the odorants according to our model. FIG. 11A shows performance of the ~27 participants per mixture tested in Experiment 4. Small circles reflect specific mixture combinations; large circles reflect the average at a given angle distance. The solid blue line is a fit to the moving average, the red dashed line is 41.8% accuracy, or d'=1. FIG. 11B shows performance of all participants from both studies combined (Bushdid and Experiment 4) at triangle tasks as a function of angle distance. The solid blue line is a fit to a moving average, the red dashed line is 41.8% accuracy, or d'=1. FIG. 11C shows performance in Experiment 5, the same-different task, plotted as a function of angle distance. Small circles reflect specific mixture combinations; large circles reflect the average at a given angle distance. Solid blue line is a fit to the moving average, the red dashed line is d'=1. FIG. 11D shows performance in Experiment 5 displayed by individual participant rather than by odorant comparison, sorted by performance. Color codes indicate subject performance accuracy. d'=1 is color coded in white, red is d'<1, blue is d'>1.

To generate a deciding value, we combined all the data across both studies (ours and Bushdid's), and observe a JND of 0.026 radians (FIG. 11B). This conclusion, however, has some limitations. First, our experiments (but not Bushdid's) were conducted at one concentration per mixture. This may allow for intensity cues or trigeminality to aid and impact discrimination scores. Second, and more importantly, triangle experiments are not the method of choice for determining JNDs because they have an inherent memory component that may also impact results. Indeed, in color discrimination tasks performance drops to astonishingly low levels if the colors are presented in succession rather than simultaneously, yet in olfaction, different odorants cannot be presented simultaneously. To address these issues we set out to perform Experiment 5 where 30 participants conducted a total of 12,000 trials of a two-alternative same-different task. This task design is easier for subjects to perform, and allows deriving the JND with greater statistical power and one reason for this is that unlike in the triangle task, we now have trials denoted "correct rejection", allowing for a more traditional derivation of d' in comparison to its derivation in the triangle task). We used 50 pairs of odorant mixtures differing by 0.0125, 0.025, 0.05, 0.1, 0.2 radians, 10 different pairs for each value. Moreover, each odorant was used at two different concentrations in order to prevent intensity cues. On each experiment each participant conducted 400 trials (spread across 8 days), which on average contained half "same" and half "different" mixture pairs. We again observed that d' increased as angle distance increased ($F(4.29)=17.07$, $p<0.0001$) (FIG. 11C), thus again verifying the validity of our measure and new model in yet another novel data set. Moreover, despite variability across participants (FIG. 11D), we observed that all angle distances above 0.0125 radians in the new same-different task had a d' that was significantly above "1" (all mean>1.38, all t>2.5, all p<0.02), yet for angle distance=0.0125, d' was under, but not significantly different from "1" (mean value=0.97, t=0.29, p=0.77) (FIG. 11C). Taken together, these massive sets of data combine to imply a human odor quality JND at an angle distance of 0.0125 radians in odorant physicochemical space (FIG. 11C).

The present embodiment thus comprises two steps: First, we develop a physicochemical measure of smell that is applicable to real-world odorant mixtures, predicting their perceptual similarity from their structure alone. Second, we use this measure to uncover the odor quality JND. The combination of these two steps may have significant impact in neurobiology, technology, and society.

For neurobiology, the measure provides for a systematic framework to probe the olfactory system. To date, such probing was limited by two factors: how stimuli were constructed, and how they were ordered. First, as to how stimuli were constructed, most of the field studied the brain response to monomolecules. Monomolecules don't exist in nature, or in other words, we have been characterizing the brain response to a stimulus that the brain did not evolve to decode. The brain evolved to decode odorant mixtures, and here we provide for a framework to systematically generate such mixtures. Second, as to how stimuli were ordered, scientists often used standard chemical groupings, whether carbon chain-length, functional group, etc., to order their stimuli. However, as noted in a lecture by the late Larry Katz, "the olfactory system did not evolve to decode the catalogue of Sigma-Aldrich", or in other words, also in the case of stimulus ordering, we have been characterizing the brain response to an order that the brain did not evolve to decode. The current framework orders odorant mixtures by a physicochemical measure that reflects perceptual similarity, and in this provides for biologically (not chemically) plausible ordering of stimuli. Thus, we provide for a perceptually inspired framework of stimuli that are realistically constructed (mixtures) and realistically ordered (by similarity). Whereas the above reflects neurobiological implications of the measure, there are also implications for the JND itself. The JND determines the minimal sensitivity that olfactory receptors and circuits must have. This will impact both experimentation and neural modeling of olfaction. Finally, a frustrating limitation that we and others who have built olfactory models have experienced is that even when one generates a reproducible rule linking an aspect of odorant structure to an aspect of odorant perception (an example of this is the many converging models linking odorant structure to odorant pleasantness), these rules fail to gain traction outside of the small community that generated them. This is primarily because implementing these models often calls for a level of computational sophistication that may deter potential users.

Beyond neurobiology, the current effort may have significant implications for technology, and specifically for the highly sought prize of digitizing smell. The JND we uncovered (0.0125 radians) provides for yet additional evidence of an exquisite sense of smell in humans (13, 27-30). Whereas this can be perceived as a form of good news, it's in fact bad news for odor digitization efforts. Such digitization depends on the combination of an odor recorder such as the electronic nose or eNose of the present embodiments, a digital code, and an odor emitter (currently typically referred to as olfactometers). Our results imply that both the recorder and emitter will need sensitivity of at least 0.0125 radians in order to achieve faithful recreation of an olfactory scene. Whereas this resolution may be within reach of current sensing technology, we know of no odor emitter that can get even close. Thus, the JND implies that faithful digitization of smell, at least in the sense of an emitted odor that is indiscriminable from the recorded odor, may be impossible. In turn, indiscriminability may be too high an order for digitization in the first place. Under this assumption, the current measure of smell may in fact aid digitization, as it allows for estimating the perceptual distance between a recreated odorant and its target odor, or in other words, may provide a framework for odorant compression.

Finally, the olfactory JND may have meaningful societal implications. The perfume industry is a multi-billion-dollar establishment that is notoriously secretive.

Successful perfume formulas were closely guarded as trade secrets, often the material of emotional legal battles. This reliance on secrecy, however, was challenged by the advent of modern analytical methods, particularly gas-chromatography mass-spectrometry (GCMS). The latter allowed relatively easy reverse-engineering of any scent formula. With the loss of secrecy, the perfume industry is turning to legal protection of trademarks, patents, and copyright. Whereas trademarking is relatively straightforward, both patents and copyright of scents have a major limitation: one can potentially patent or copyright a formula (a list of ingredients at specific ratios), but how can one patent its resultant smell? Indeed, if one were to patent or copyright the formula, one would be forced to make it public. This would allow others to take the formula, replace ingredients with different similarly smelling ingredients, and thus obtain the same end smell without infringing on the patent or copyright. This has indeed prevented most perfume companies from taking the patent/copyright path. The current measure and JND potentially change all this. Now one can potentially claim a novel odor composition in terms of its location in olfactory space, and any point within quality JND of this location can be said to violate the patent or copyright, regardless of its molecular content. As a case study highlighting the problematic current state, and how the JND can change this, we can use the iconic odor of Chanel No. 5®, the best-selling perfume in history. Its formula was of course never published, but we can use one of the many takeoffs that have been. The formula we use has 12 components, and we will call it Imitation Chanel No. 5. We can now use our measure and JND to replace each component with a different component, and balance these replacements such that the end mixture, that we will call Ravia No. 5, is within 0.0119 radians of Imitation Chanel No. 5. Thus, Ravia No. 5 is a computer-generated perfume that has zero % chemical overlap with Imitation Chanel No. 5 (no molecules in common), and which thus under current laws does not infringe on any intellectual property, yet it smells exactly the same as Imitation Chanel No. 5. In contrast, we can again use our measure to merely shift the relative proportion/intensity of only one component in Imitation Chanel No. 5®, and balance this such that the end mixture, that we will call LV No. 5, is 0.2 radians of Imitation Chanel No. 5. Thus, LV No. 5 is a computer-generated perfume that has 100% chemical overlap with Imitation Chanel No. 5 (all molecules in common), and which thus under current laws likely infringes on intellectual property, yet it smells nothing like Imitation Chanel No. 5. We should note that a non-perfume equivalent of this example already exists in our data, e.g., the odorant pairs #86 vs #96, or #88 vs #98 in Supplementary Data 3, cases of mixtures with zero % chemical overlap, but within 0.0125 radians, and indeed an identical (indiscriminable) smell). This demonstration depicts both the current problematic state of odor-related intellectual property, and how the odor quality JND can change this. Thus, we conclude that beyond obvious impact on olfactory neurobiology and odor technology, the olfactory JND may also gain meaningful impact on society.

Experimental Details for the JND

Methods

Participants: In total 166 participants (105 women), aged 19-42 participated in the 5 experiments conducted here. Some participated in more than one type of experiment, as data collection for the experiments herein lasted for about four years. Participants were all in general good health, with no reported history of neurological or mental illness, and neither olfactory deficits nor chronic or acute conditions that involved the respiratory tracts. All participants provided written informed consent to procedures approved by the Weizmann Institute IRB Committee, and all participants were paid for participation.

Location: All experiments were conducted in rooms specially constructed for human olfaction experiments in the Olfaction Lab at Weizmann Institute. These rooms are coated in stainless-steel in order to prevent odor adhesion over time, and are subserved by rapid air exchange with humidity and temperature control, as well as HEPA and carbon filtration. All this promises to minimize cross-trial contaminations.

Odorants: All discrimination tasks were conducted using odorant mixtures. All mixtures but three, were prepared specifically for these experiments, using 148 monomolecular components (see Supplementary Data 1). All mixtures recipes are in Supplementary Data 2. Three mixtures were prepared to imitate the odors of rose, violet and asafoetida. Mono-molecules were purchased from Sigma-Aldrich. All odorants were diluted with either 1,2-Propanediol or isopropyl myristate (IPM).

Tasks: In all tasks participants were alone in the experimental room, monitored from an adjacent control room. All interactions were computer controlled: selection of jars to sniff was by computer commend, and ratings were inputted by computer mouse that was used to either mark a visual analogue scale (VAS) or select correct answers. Intensity and similarity experiments were ran on an internal website coded in Dropal. The Discrimination experiments (Triangle tasks and Same-different tasks) were coded and ran in MATLAB, using the Psychophysics Toolbox extensions (35-37). All experimental sessions were limited to one hour at the most, and were continued across days.

Intensity Ratings: On each trial the participant received an arbitrarily marked sniff jar. The participant was instructed to sniff the jar once, and then enter their perceived intensity rating on a VAS. Inter-trial-interval (ITI) was 30 seconds. Odor order was randomized.

Similarity ratings: On each trial the participant received two arbitrarily marked sniff jars. The participant was instructed to sniff them by predetermined order (counter balanced across participants), and then enter their perceived similarity rating on a VAS. ITI was 40 seconds.

Triangle Task: On each trial the participant received three arbitrarily marked sniff jars, two containing an identical odorant mixture, and one containing a different odorant mixture. The participants were permitted only one sampling per odorant, and were instructed to select the odd odorant. Inter-stimulus-interval was self-paced, and ITI was >30 seconds (added variability reflecting trial time).

Same-Different Task: On each trial the participant received two arbitrarily marked sniff jars, containing either identical or different odorant mixtures. The participants were permitted unrestricted sampling per odorant, and were instructed to determine whether the pair was "same" or "different". Inter-stimulus-interval was self-paced, and ITI was >30 seconds.

Obtaining chemical descriptors: For each odorant, 4,885 physicochemical descriptors were calculated using DRAGON software. Out of these descriptors, 21 descriptors (see Supplementary Table 1) that were previously shown to be efficient for mixture modeling were extracted. Because the descriptors measure properties on different scales, each of the 21 descriptors was then normalized to a 0-1 continuous scale. This was done as follows; the list of values vd was extracted for each descriptor. The minimum and maximum value for each descriptor was found in a list of 4,064 molecules that were descripted to have a smell. For each odor the normalized value on that descriptor was computed as:

$$\frac{v - \min(vd)}{\max(vd) - \min(vd)}.$$

Then the maximal value for an odor on that descriptor was exactly 1, and the minimal value was exactly 0 and other odors had a value in between. A vector of length 21, each valued between 0 and 1, then represented each odor.

Modeling Mixtures: Each mixture was modeled as a weighted vector summation of its components, making a new 21-dimensional representation of each mixture. The weights for each of the mono-molecules were determined according to their perceived intensities. The function that converts perceived intensity to vector weights was assumed to be psychometric in the form of $$\frac{1}{1 + e^{-\frac{x-\alpha}{\beta}}}$$

Its parameters were fitted using the data of experiment 1.

Distance between odors: The distance function between the vector representing mixture $\vec{u}$ and the vector representing mixture $\vec{v}$ was computed as the angle between them in the 21-dimensional space. It was given by:

$$\theta(\vec{u}, \vec{v}) = \arccos\left(\frac{\vec{u} \cdot \vec{v}}{|\vec{u}| \cdot |\vec{v}|}\right)$$

where $\vec{u} \cdot \vec{v}$ is the dot product between the vectors and $|\vec{u}|$ and $|\vec{v}|$ are their Euclidean norms.

Statistical Analysis

All statistical analysis was conducted in MATLAB Release 2017b of The MathWorks, Inc., Natick, Mass., United States.

Density estimation: All density estimations for graphical purposes were performed using kernel methods (Epanechnikov kernel).

Pearson's Correlation coefficient: All correlations referred to in this manuscript are Pearson's correlation coefficients. The p-values derived from them are tested against the Ho hypothesis that the correlation equals zero.

Calculating correlations with or without comparisons of identical mixtures: In estimating the prediction of perceived similarity from angle distance we can calculate the correlation either with (red lines in the figures) or without (black lines in the figures) comparisons between identical mixtures. There are arguments for either path: In generating predictions of perceived similarity from odorant structure, we are trying to capture two sources of variance: the difference between people and the difference between molecules. One could argue that in comparisons between identical mixtures, we have negated the variance associated with molecules, and therefore we should not consider this correlation. This would be unarguable had people consistently rated the perceptual similarity of identical mixtures at 100%, or at minimum, always rated the perceptual similarity of identical mixtures as the same. Neither of these outcomes, however, occurred. Thus, one may argue that including these comparisons is informative for capturing the representation of olfactory perceptual space. In any case, in the present embodiments we present both outcomes, and notably put up front the method that in fact diminishes the impact of our new algorithm. In other words, we highlighted the less rewarding outcome.

Performance estimation in the triangle task: To estimate the performance on the triangle test as a function of the angle distance, we sorted the data according to the computed angle distance, and used a moving average method to estimate performance at each point. Then a cubic interpolation was performed in order to generate a continuous function. Because the triangle test requires a relatively large number of trials in order to achieve satisfying statistical power, we used 47 trials per point estimation.

Derivation of d-prime: In order to analyze the forced choice experiments we used methods from signal detection theory. The d-prime (d') is a standard measure for the discriminability of two different stimuli. One advantage of using d' is that it is consistent between different paradigms, and allows comparing different discrimination tasks.

Data Availability

All raw behavioral data is published as supplementary material. All the odorants used are in Data File #1, all behavioral similarity results are in Data File #2, all behavioural discrimination results are in Data File #3.

Reference is now made to FIGS. 12A and 12B which show the odorants used projected into perceptual space. FIG. 12A relates to the 148 molecules used across experiments overlaid on 4046 molecules within the first and second Principal Components of physicochemical space. FIG. 12B shows the molecules within the first and second Principal Components of perceptual space. Shown is perceptual space data for only 470 molecules as background, and these contain 115 of the 148 molecules we used. The present combination implies that the odorant molecules we used for our mixtures provided an effective span of both physicochemical and perceptual spaces.

Reference is now made to FIGS. 13A-13D which illustrate correlation between angle distance and perceived similarity.

Figure 13B:
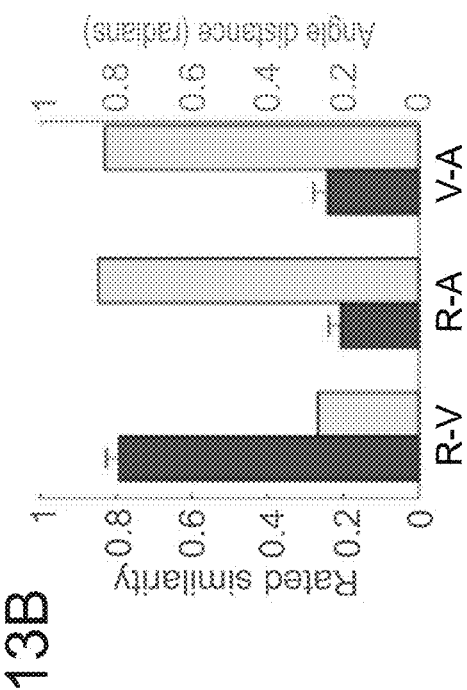
Figure 13D:
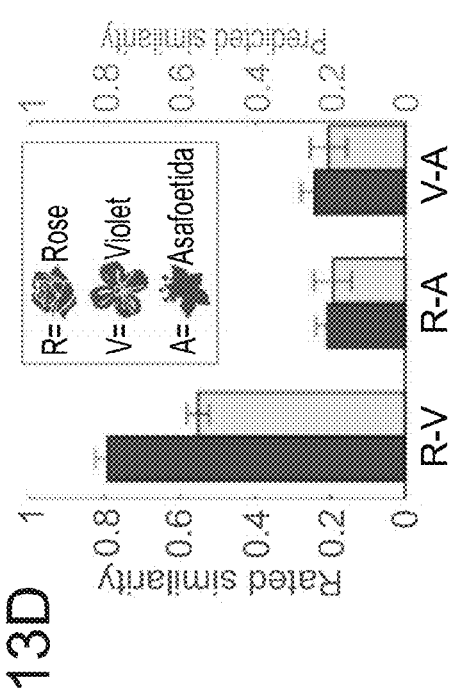
Figure 13A:
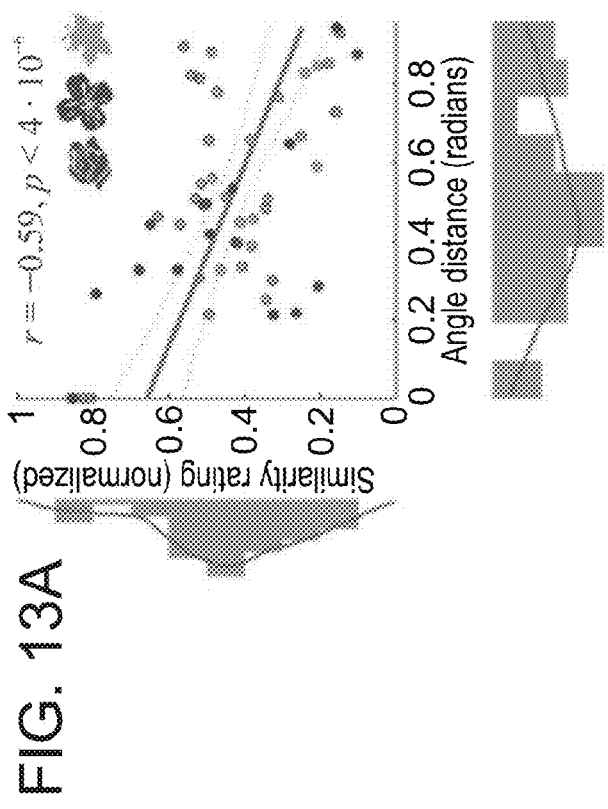
Figure 13C:
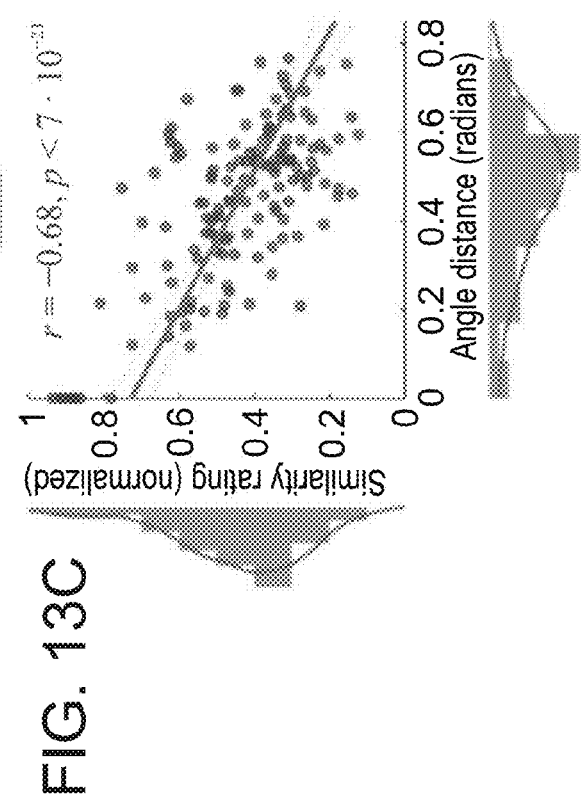

FIGS. 13A-C are scatter plots where each dot is a pairwise comparison of two odorants, on the Y axis their actual similarity as rated by participants, and on the X axis their distance according to the model. FIG. 13A shows data from the experiment containing rose, violet, asafoetida, and 11 additional odorant mixtures. All comparisons containing rose are shown in red, all comparisons containing violet are indicated in violet, and all comparisons containing asafoetida are shown in mustard (n=30).

FIG. 13B shows rated similarity vs. angle distance between rose, violet, and asafoetida comparisons in this experiment. FIG. 13C shows data from Experiments 1 and 2 used for model building. FIG. 13D shows the end result of predicted vs. actual similarity of rose, violet, and asafoetida.

In the above experiments, angle distance is directly related to perceived similarity, but the exact transform of this link cannot be deterministically formulated, as its reporting by participants is completely context dependent. By analogy, consider the link between wavelength and perceived similarity in the color of light. Assume we want to estimate the perceptual similarity of two stimuli: 575 nm versus 595 nm. We provide participants with pairwise comparisons of lights. In Experiment 1 we use the following 6 pairs of stimuli (all in nm): 519-520; 575-577; 580-581; 575-595; 600-601; 610-612. Participants in this experiment likely rate the perceptual similarity of the 575-595 pair as very low, because it is the least similar pair they will encounter in the experiment. By contrast, in an experiment where the stimuli pairs are: 519-620; 475-577; 480-581; 575-595; 500-601; 510-612, participants will likely rate the perceptual similarity of the 575-595 pair as very high, because it is the most similar pair they will encounter in the experiment. In other words, the link between the reported similarity of a pair of odorant is on one hand determined by their angle distance, but this is scaled by the other pairs of odorants in the experiment.

Thus, to transform from angle distance (FIG. 13B) to perceived rated similarity (FIG. 13D), we go through the particular set of odorants they were combined with (FIG. 13A). Here this is the three-step calculation:

(1) We first calculated the angle distance for the 3 pairwise mixture comparisons of experiment 3.

(2) We then used a linear model to predict the perceived intensity per angle distance, based on the results of both experiments 1 and 2 (FIG. 13C). Confidence intervals were also derived from the linear model estimation.

(3) We applied this model on the 3 pairwise angle distances obtained in FIG. 13A. Finally, to relate these ratings to the scale of ratings used in experiment 3, data was normalized between the minimal and maximal similarity values obtained throughout the experiment for comparisons, which involved the three odors used in experiment 3 (rose, violet and asafoetida) (FIG. 13A). This resulted in predicted similarity value between 0-1 (FIG. 13D). The bottom line of all this is that our model will always predict that the pairwise difference between rose and violet is 0.27 radians, rose and asafoetida is 0.85 radians, and violets and asafoetida is 0.83 radians. This is deterministic. But the transform from this to a reported similarity score ranging from 0 to 1 is a function of the other odorants in the experiment.

SUPPLEMENTARY TABLE 1

Descriptors used for optimized angle model, from ref. (10)

| No. | Index out of 4885 descriptors | Abbreviation | Descriptio |
|---|---|---|---|
| 1 | 45 | nCIR | Number of circuits (constitutional descriptors). |
| 2 | 76 | ZM1 | First Zagreb index M1 (topological descriptors). |
| 3 | 97 | GNar | Narumi geometric topological index (topological descriptors). |
| 4 | 122 | S1K | 1-path Kier alpha-modified shape index (topological descriptors). |
| 5 | 187 | piPC08 | Molecular multiple path count of order 08 (walk and path counts). |
| 6 | 936 | MATS1v | Moran autocorrelation-lag 1/weighted by atomic van der Waals volumes (2 D autocorrelations). |
| 7 | 942 | MATS7v | Moran autocorrelation-lag 7/weighted by atomic van der Waals volumes (2 D autocorrelations). |
| 8 | 984 | GATS1v | Geary autocorrelation-lag 1/weighted by atomic van der Waals volumes (2 D autocorrelations). |
| 9 | 1492 | Eig05_AEA(bo) | Eigenvalue n. 5 from augmented edge adjacency mat. weighted by bond order. |
| 10 | 1356 | SM02_AEA(bo) | Spectral moment of order 2 from augmented edge adjacency mat. weighted by bond order. |
| 11 | 1371 | SM03_AEA(dm) | Spectral moment of order 3 from augmented edge adjacency mat. weighted by dipole moment. |
| 12 | 1378 | SM10_AEA(dm) | Spectral moment of order 10 from augmented edge adjacency mat. weighted by dipole moment. |
| 13 | 1381 | SM13_AEA(dm) | Spectral moment of order 13 from augmented edge adjacency mat. weighted by dipole moment. |
| 14 | 1103 | SpMin3_Bh(v) | Smallest eigenvalue n. 3 of Burden matrix weighted by van der Waals volume Burden eigenvalues. |
| 15 | 1806 | RDF035v | Radial Distribution Function-035/weighted by van der Waals volume. |
| 16 | 2191 | G1m | $1^{st}$ component symmetry directional WHIM index/weighted by mass. |
| 17 | 2202 | G1v | $1^{st}$ component symmetry directional WHIM index/weighted by van der Waals volume. |
| 18 | 2213 | G1e | $1^{st}$ component symmetry directional WHIM index/weighted by Sanderson electronegativity. |
| 19 | 2248 | G3s | $3^{rd}$ component symmetry directional WHIM index/weighted by 1-state. |
| 20 | 2452 | R8u+ | R maximal autocorrelation of lag 8/unweighted. |
| 21 | 2646 | nRCOSR | Number of thioesters (aliphatic). |

SUPPLEMENTARY TABLE 2

Recipes for rose, violet and asafetida, provided by Christophe Laudamiel from DreamAir LLC

| Ingredient | W | Intensity | Concentration | CID | CAS | Scent |
|---|---|---|---|---|---|---|
| Citronellol Laevo | 22 | 53 | 1 | 8842 | 106-22-9 | Rose |
| Damascenone | 0.2 | 75 | 1 | 5366074 | 23696-85-7 | Rose |
| Geraniol Pur | 2 | 50 | 1 | 637566 | 106-24-1 | Rose |
| Linalol | 25 | 60 | 1 | 6549 | 78-70-6 | Rose |
| Phen Eth Alc Pure | 30 | 40 | 1 | 6054 | 60-12-8 | Rose |
| Rose Oxyde Laevo | 0.1 | 70 | 1 | 1712087 | 3033-23-6 | Rose |
| Triplal | 0.5 | 80 | 1 | 93375 | 68039-49-6 | Rose |
| Cis-3-Hexenyl Isobutyrate | 0.6 | 70 | 1 | 5352539 | 41519-23-7 | Rose |
| Citronellyl Acetate | 8 | 45 | 1 | 9017 | 150-84-5 | Rose |
| Citral | 0.5 | 75 | 1 | 638011 | 5392-40-5 | Rose |
| Methyl Iso Eugenol | 2 | 40 | 1 | 7128 | 93-16-3 | Rose |
| Methyl Ionone Beta | 10 | 50 | 1 | 5375218 | 127-43-5 | Violet |
| Cis-3-Hexenyl Acetate @ 10% IPM | 0.2 | 60 | 0.1 | 5363388 | 3681-71-8 | Violet |
| Phenyl Ethyl Isobutyrate | 2 | 45 | 1 | 7655 | 103-48-0 | Violet |
| Linalol | 7 | 60 | 1 | 6549 | 78-70-6 | Violet |

SUPPLEMENTARY TABLE 2-continued

Recipes for rose, violet and asafetida, provided by Christophe Laudamiel from DreamAir LLC

| Ingredient | W | Intensity | Concentration | CID | CAS | Scent |
|---|---|---|---|---|---|---|
| Alpha Ionone | 20 | 55 | 1 | 5282108 | 127-41-3 | Violet |
| Geonol @ 0.01% | 0.5 | 35 | 1.00E−05 | 1213 | 23333-91-7 | Violet |
| Ionone Beta | 10 | 50 | 1 | 638014 | 14901-07-6 | Violet |
| Cis-3-Hexenol | 0.5 | 65 | 1 | 5281167 | 928-96-1 | Violet |
| Nonadienol @ 1% IPM | 0.2 | 60 | 0.01 | 34134 | 7786-44-9 | Violet |
| Glycolierral | 5 | 35 | 1 | 111418 | 68901-32-6 | Violet |
| Hedione High Cis | 20 | 35 | 1 | 102861 | 24851-98-7 | Violet |
| Meth Meth Thiopropionate | 2 | 70 | 1 | 61641 | 13532-18-8 | Asafoetida |
| PyrazoMethoxy @ 1% CITR | 0.1 | 1 | 0.01 | 520098 | 24168-70-5 | Asafoetida |
| Meth Pentenoic Acid | 1 | 45 | 1 | 18458 | 3142-72-1 | Asafoetida |
| Sulfox @ 1% DIPG | 0.2 | 65 | 0.01 | 61982 | 38462-22-5 | Asafoetida |
| Isolongifolene | 30 | 15 | 1 | 11127402 | 1135-66-6 | Asafoetida |
| IPM | 30 | 2 | 1 | 8042 | 110-27-0 | Asafoetida |
| Dimethyl Sulfide @ 1% | 0.1 | 70 | 0.01 | 1068 | 75-18-3 | Asafoetida |
| Galbanolene Super @ 10% IPM | 0.1 | 53 | 0.1 | 5367412 | 16356-11-9 | Asafoetida |
| Isovalerianic Acid @ 10% IPM | 0.2 | 50 | 0.1 | 10430 | 503-74-2 | Asafoetida |
| Phenyl Acetic Acid | 1 | 57.5 | 1 | 999 | 103-82-2 | Asafoetida |
| Benzoic acid phenylemthyl ester | | | 2345 | 8.3 | 0.7 | LV #5 |
| Benzoic acid 2-hydroxy-phenylmethyl ester | | | 8363 | 8.3 | 0.7 | LV #5 |
| (2E)-3-Phenyl-2-propen-1-ol | | | 5315892 | 8.3 | 0.7 | LV #5 |
| 2 6-Octadienal 3 7-dimethyl-(2E)- | | | 638011 | 8.3 | 0.7 | LV #5 |
| 6-Octen-1-ol 3 7-dimethyl- | | | 8842 | 8.3 | 0.7 | LV #5 |
| 2H-1-Benzopyran-2-one | | | 323 | 8.3 | 0.7 | LV #5 |
| 4-Ally-2-methoxyphenol | | | 3314 | 8.3 | 0.7 | LV #5 |
| 2 6 10-dodecatrien-1-ol 3 7 11-trimethyl- | | | 3327 | 8.3 | 0.7 | LV #5 |
| 2 6-octadien-1-ol 3 7-dimethyl- | | | 637566 | 8.3 | 0.7 | LV #5 |

Reference is now made to FIG. 14, which illustrates a digital electronic nose 40 according to the present embodiments. The digital electronic nose 40 comprises an n-dimensional digitized perception space 42, which can in fact be any model that stores perceptions of smells, typically based on odorant structure against odorant perception. The model discussed hereinabove is a suitable example. Such a model is typically built up using multiple odorant chemicals and n axes of smell. The resulting perceptual space is then digitized in terms of just noticeable distances, and the just noticeable distances are an average of minimum discernable distances over a group of users.

The nose has an input 41 that includes chemical sensors in order to sense the odor to be measured. A mapping unit 44 is connected to the input and to the n-dimensional digitized perception space, and uses outputs of the chemical sensors to map the input odor onto a location on the digitized n-dimensional perception space. The location is expressed digitally in terms of the just noticeable distances.

An output 46 then outputs a digitized measurement of the input odor based on the location as expressed in terms of the just noticeable distances. The output may be to another machine, in which case the digital characterization may be utilized directly, or the output may be to a human, in which case natural language representations of the odor may optionally be used.

The n-dimensional perception space may be electronically stored within the nose. For example it may be hardwired, say into a ROM, or it may be stored in volatile manner in a RAM, or it may be held in flash memory, or in any other suitable form.

The n-dimensional perception space may comprise physicochemical descriptors applied to molecules along n axes of smell, wherein n is a plural integer, say 18 or 22.

The respective just noticeable distances are angles on the n-dimensional perception space. For the particular perception space used herein, the just noticeable distances ranged between 0.02 radians and 0.14 radians, depending on the human subjects, with an average, the value adopted here, of 0.051 radians.

The angle between two odors on the n-dimensional digitized perception space may be defined as $$\arccos\left(\frac{\vec{u} \cdot \vec{v}}{|\vec{u}| \cdot |\vec{v}|}\right)$$

where $\vec{u} \cdot \vec{v}$ is the dot product between vectors representing said two odors respectively and $|\vec{u}|$ and $|\vec{v}|$ are their Euclidean norms.

The molecules in the perception space may be weighted according to $$W(X) = \frac{1}{1 + e^{-\frac{x-1.3}{0.07}}}$$

where x is a normalized intensity.

Reference is now made to FIG. 15, which shows an embodiment 50 of an enose in which no perception space or sample space is used. Instead, a sample is detected at input 52 by the enose chemical input sensors and when two odors have been sampled, a distance may be measured between them, at measurement unit 54, using a direct enose similarity calculation, meaning that the similarity is based directly on the enose input sampling. This embodiment may be used to produce analog measurements as in the first embodiment, or the measures may be digitized according to the digital embodiments. Output may be provided as a measurement or using descriptors, as discussed above.

It is expected that during the life of a patent maturing from this application many relevant electronic noses and other odor sampling technologies will be developed and the scope of the terms electronic nose and enose are intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of assessing odors, comprising:
   providing an electronic nose that extracts measurements from odors, from which measurements at least n chemical descriptors are extractable where n is greater than unity;
   applying said electronic nose to an odor;
   extracting odor information of said odor using said electronic nose;
   plotting said extracted odor information to a first location in an n-dimensional sample space, each dimension being related to a respective one of said n chemical descriptors; and
   outputting an assessment based on said first location, said outputting an assessment comprising outputting details of one or more odor-carrying chemicals having regions on or close to said first location, wherein said n-dimensional sample space comprises physicochemical descriptors applied to molecules along n axes of smell, wherein n is a plural integer and said molecules in said perception space are weighted according to $$w(x) = \frac{1}{1 + e^{-\frac{x-1.3}{0.07}}}$$

where x is a normalized intensity.

2. The method of claim 1, comprising selecting said n chemical descriptors from m chemical descriptors available from said electronic nose, where m is greater than n.

3. The method of claim 2, comprising selecting said n chemical descriptors that build a sample space on which test odors identified to be similar cluster relatively close together and test odors identified to be different are relatively far apart.

4. The method of claim 1, said sample space having a plurality of regions, the method comprising associating respective regions of said sample space with corresponding odor describing terms, and said outputting an assessment comprises outputting an odor describing term associated with said first location.

5. The method of claim 4, wherein said regions are locations in said sample space of test odors and wherein said terms are terms associated with said test odors.

6. The method of claim 1, comprising providing templates for odor-related discourse, and inserted said odor-describing term associated with said first location into one of said templates.

7. The method of claim 1, said sample space having a plurality of regions, the method comprising:
   associating respective regions of said sample space with corresponding odor carrying chemicals, and said outputting an assessment comprises outputting details of one or more odor-carrying chemicals having regions on or close to said first location.

8. The method of claim 7, comprising synthesizing said odor using said odor-carrying chemicals defined in said details.

9. The method of claim 1, wherein n is 18.

10. The method of claim 1, comprising building an n-dimensional perception space.

11. The method of claim 10, comprising finding a just noticeable distance between odors on said perception space, said just noticeable distance being an average of minimum discernable distances over a group of users.

12. The method of claim 11, comprising digitizing said perception space based on said just noticeable distances.

13. The method of claim 11, comprising using said digitizing to provide a measurement of an input odor.

14. The method of claim 11, comprising using said digitizing to provide a comparison between different odors.

15. A method of assessing odors, comprising:
   providing an electronic nose that extracts measurements from odors, from which measurements at least n chemical descriptors are extractable where n is greater than unity;
   applying said electronic nose to an odor;
   extracting odor information of said odor using said electronic nose;
   plotting said extracted odor information to a first location in an n-dimensional sample space, each dimension being related to a respective one of said n chemical descriptors, said sample space having a plurality of regions;
   associating respective regions of said sample space with corresponding odor carrying chemicals, wherein said n-dimensional sample space comprises physicochemical descriptors applied to molecules along n axes of smell, wherein n is a plural integer and said molecules in said perception space are weighted according to $$w(x) = \frac{1}{1+e^{-\frac{x-1.3}{0.07}}}$$

where x is a normalized intensity;
outputting an assessment based on said first location; and
selecting a predetermined number of most commonly occurring odor describing terms, wherein said predetermined number is at least 5, said sample space having a plurality of test samples plotted thereon, each sample being associated with at least one odor describing term, the method comprising finding a predetermined number of closest test samples to said first location or finding all test samples within a predetermined radius of said first location and said outputting an assessment comprises outputting an odor describing term associated with said test samples thus found.

16. The method of claim 15, comprising selecting a predetermined number of most commonly occurring odor describing terms.

17. The method of claim 16, wherein said predetermined number is 5.

18. A digital electronic nose comprising:
an n-dimensional digitized perception space, the space digitized as just noticeable distances, said just noticeable distances being an average of minimum discernable distances over a group of users, and wherein n is at least five;
an input for an odor to be measured;
a mapping unit connected to said input and to said n-dimensional digitized perception space, for mapping said input odor into a first location on said digitized n-dimensional perception space, said first location being expressible digitally in terms of said just noticeable distances, wherein said n-dimensional perception space comprises physicochemical descriptors applied to molecules along n axes of smell, wherein n is a plural integer and said molecules in said perception space are weighted according to $$w(x) = \frac{1}{1+e^{-\frac{x-1.3}{0.07}}}$$

where x is a normalized intensity;
an output for outputting a digitized measure of said input odor based on said first location expressed in terms of said just noticeable distances.

19. The digital electronic nose of claim 18, wherein said n-dimensional perception space is electronically stored.

20. The digital electronic nose of claim 18, wherein respective just noticeable distances are angles on said n-dimensional perception space.

21. The digital electronic nose of claim 20, wherein an angle between two odors on said n-dimensional digitized perception space is $$\arccos\left(\frac{\vec{u} \cdot \vec{v}}{|\vec{u}| \cdot |\vec{v}|}\right)$$

where $\vec{u} \cdot \vec{v}$ is the dot product between the vectors representing said two odors respectively and $|\vec{u}|$ and $|\vec{v}|$ are their Euclidean norms.

22. A method of assessing odors, comprising:
providing an electronic nose that extracts chemical characterizations from odors;
applying said electronic nose to first and second odors;
extracting a chemical odor characterization of said first and second odors respectively using said electronic nose;
finding a just noticeable distance between odors on said perception space, said just noticeable distance being an average of minimum discernable distances over a group of users;
measuring a distance between respective chemical odor characterizations of said first and second odors in an n-dimensional space digitized according to said just noticeable distance, wherein said n-dimensional space comprises physicochemical descriptors applied to molecules along n axes of smell, wherein n is a plural integer and said molecules in said perception space are weighted according to $$w(x) = \frac{1}{1+e^{-\frac{x-1.3}{0.07}}}$$

where x is a normalized intensity; and
outputting said distance as a measure of similarity between said first and second odors.

23. The method of claim 22, comprising digitizing said distance in terms of just noticeable differences.

* * * * *